US012295656B2

(12) United States Patent
Dubois et al.

(10) Patent No.: US 12,295,656 B2
(45) Date of Patent: May 13, 2025

(54) COMPOSITE OCULAR BLOOD FLOW ANALYZER

(71) Applicant: OCUFLOW LLC, Glen Arm, MD (US)

(72) Inventors: Robert Ogden Crane Dubois, Glen Arm, MD (US); Theresa Retue Kramer, Glen Arm, MD (US); Rhonda Richardson Grebe, Abingdon, MD (US); Paul Joseph Howell, Cumberland, ME (US)

(73) Assignee: OCUFLOW, INC., Glen Arm, MD (US)

( * ) Notice: Subject to any disclaimer, the term of this patent is extended or adjusted under 35 U.S.C. 154(b) by 1345 days.

(21) Appl. No.: 15/053,063

(22) Filed: Feb. 25, 2016

(65) Prior Publication Data

US 2017/0245751 A1    Aug. 31, 2017

(51) Int. Cl.
| | |
|---|---|
| *A61B 3/00* | (2006.01) |
| *A61B 3/10* | (2006.01) |
| *A61B 3/16* | (2006.01) |
| *A61B 5/00* | (2006.01) |
| *A61B 5/022* | (2006.01) |
| *A61B 5/0295* | (2006.01) |
| *A61B 5/021* | (2006.01) |

(52) U.S. Cl.
CPC .......... *A61B 3/0025* (2013.01); *A61B 3/0041* (2013.01); *A61B 3/10* (2013.01); *A61B 3/16* (2013.01); *A61B 5/0024* (2013.01); *A61B 5/02216* (2013.01); *A61B 5/02225* (2013.01); *A61B 5/0295* (2013.01); *A61B 5/7225* (2013.01); *A61B 5/021* (2013.01); *A61B 5/4088* (2013.01)

(58) Field of Classification Search
CPC .............................. A61B 3/16; A61B 5/02216
See application file for complete search history.

(56) References Cited

U.S. PATENT DOCUMENTS

| | | |
|---|---|---|
| 3,099,262 A | 7/1963 | Bigliano |
| 3,102,534 A | 9/1963 | Bigliano et al. |
| 3,299,882 A | 1/1967 | Masino |

(Continued)

FOREIGN PATENT DOCUMENTS

| | | |
|---|---|---|
| EP | 0 315 329 | 10/1989 |
| JP | H01-280441 | 11/1989 |

(Continued)

OTHER PUBLICATIONS

Instruction Book for the Langham OBF Computerized Tonometer Feb. 2003 Langham Ophthalmic Technologies.

(Continued)

*Primary Examiner* — Tse W Chen
*Assistant Examiner* — Michael A Catina
(74) *Attorney, Agent, or Firm* — WILSON SONSINI GOODRICH & ROSATI

(57) ABSTRACT

A composite ocular blood flow analyzer uses pneumatic tonometric techniques and structures to produce accurate, stable, and repeatable readings of intraocular pressure. A computer processes the intraocular pressure readings to produce data relating to various aspects of ocular blood flow that can be used diagnostically to identify abnormalities in the eye and other parts of the body.

94 Claims, 27 Drawing Sheets

(56) References Cited

U.S. PATENT DOCUMENTS

| | | | | |
|---|---|---|---|---|
| 3,934,462 | A * | 1/1976 | Rende | A61B 3/16 600/405 |
| 3,948,248 | A * | 4/1976 | Zuckerman | A61B 3/165 600/457 |
| 4,249,825 | A | 2/1981 | Shapiro | |
| 4,747,296 | A * | 5/1988 | Feldon | A61B 3/16 324/130 |
| 4,860,755 | A * | 8/1989 | Erath | A61B 3/16 600/405 |
| 4,883,056 | A | 11/1989 | Langham | |
| 5,715,826 | A * | 2/1998 | Horrocks | A61B 5/02007 600/485 |
| 5,830,139 | A * | 11/1998 | Abreu | A61B 3/1241 600/405 |
| 5,857,969 | A * | 1/1999 | Massey | A61B 3/16 600/398 |
| 6,314,980 | B1 | 11/2001 | Beswick et al. | |
| 6,699,198 | B2 | 3/2004 | Numajiri | |
| 7,481,767 | B2 | 1/2009 | Luce | |
| 7,909,765 | B2 | 3/2011 | Luce | |
| 7,959,570 | B2 | 6/2011 | Enikov et al. | |
| 8,602,556 | B2 | 12/2013 | Imamura | |
| 8,714,743 | B2 | 5/2014 | Verdooner | |
| 2004/0230124 | A1* | 11/2004 | Querfurth | A61B 3/16 600/485 |
| 2009/0131811 | A1* | 5/2009 | Morris | A61B 5/091 600/538 |
| 2010/0049075 | A1* | 2/2010 | Bolger | A61B 3/113 600/544 |

FOREIGN PATENT DOCUMENTS

| | | |
|---|---|---|
| JP | H10-509890 | 9/1998 |
| WO | WO 96/16589 | 6/1996 |

OTHER PUBLICATIONS

Photographs of Predicate Devices.
Langham, Maurice E., "The Applications of the Alcon Pneumatonograph to Clinical Opthalmology," pp. 1-66, 1974, Alcon Laboratoies, Fort Worth Texas.
Paradigm Blood Flow Analyzer, pp. 98-138, Paradigm Medical Industries. Inc., Salt Lake City, Utah, www.paradigm-medical.com.
Paradigm Medical Industries, Inc.—510k Submission, pp. 1-7.
Langham, Maurice E., "Ischemia and Loss of Vascular Autoregulation in Ocular and Cerebral Diseases, A New Perspective," Springer Science+Business Media, LLC New York, NY 2009, pp. xi-xiv and 1-192.
Tonoplus+ User Guide, Portable Ophthalmic Devices, Inc., Bettendorf Iowa, 2005, pp. 1-32.
Langham, ME, and Mccarthy E,, "A rapid pneumatic applanation tonometer: Comparative findings and evaluation". Arch Ophthalmol 1968;79;389-399.
Armaly, MF, "On the distribution of applanation pressure. I. Statistical features and the effect of age, sex, and family history of glaucoma," Arch Ophthalmol, 1965:73:11-18.
Schmetterer L, Kiel JW (editors). "Ocular Blood Flow," Springer-Verlag Berlin Heidelberg, Heidelberg New York Dordrecht London, 2012, pp. 1-457.
Whitacre M, Stein R. "Sources of error with use of Goldmann-type tonometers," Surv Ophthalmol 1993;38(1):1-30.
Langham ME, Farrell RA, O'Brien VO, Silver DM, Schilder P. "Blood flow in the human ey,". Acta Ophthalmologica 1989:191(Suppl):9-13.
Oppenheim B, Dickersin K, Min YI, Schockett S (1993) "Reliability of measurements using the Langham ocular blood flow system," Invest Ophthalmol Vis Sci 1993:34 [Suppl]:940.
Spraul C, Lang GE, Ronzani M, Hogel J, Lang GK. "Reproducibility of measurements with a new slit lamp mounted ocular blood flow tonograph," Graefe's Arch Clin Exp Ophthalmol 1998;236:274-279.
Walker RE and Litovitz TL, "An Experimental and Theoretical Study of the Pneumatic Tonometer," Exp. Eye Res., 1972, 13:14-32.
Walker RE and Langham ME, "Pneumatic applanation tonometer studies. III. Analysis of the floating tip sensor," Exp Eye Res 1975;20:167-172.
Walker RE, Compton GA, Langham ME, "Pneumatic applanation tonometer studies. IV. Analysis of pulsatile response," Exp Eye Res 1975;20:245-253.
Walker RE, Litovitz TL, and Langham ME, "Pneumatic applanation tonometer studies. II. Rabbit cornea data," Exp Eye Res 1972;13:187-193.
Zion IB, Harris A, Siesky B, Shulman S, McCranor, Garzozi HJ, "Pulsatile ocular blood flow: relationship with flow velocities in vessels supplying the retina and choroid," Br J Ophthalmol 2007;91:882-884.
Eisenlohr JE, Langham ME, Maumenee AE, "Manometric studies of the pressure-volume relationship in living and enucleated eyes of individual human subjects." Br J Ophthalmol 1962;46:536-548.
Silver DM and Farrell RA, (1994), "Validity of pulsatile ocular blood flow measurements," Surv Ophthalmol 1994;38:S72-S80.
Silver DM and Geyer O, "Pressure-volume relation for the living human eye," Curr Eye Res 2000;20(2):115-120.
Schmetterer L, Dallinger S, Findl O, Eichler H-G, Wolzt M, A comparison between laser interferometric measurement of fundus pulsation and pneumotonometric measurement of pulsatile ocular blood flow. Eye 2000;14:39-45.
Berisha F, Findl O, Last M, Kiss B, Schmetterer L, "A study comparing ocular pressure pulse and ocular fundus pulse in dependence of axial length and ocular volume," Acta Ophthalmoligica 2010;88:766-772.
Harris A, Jonescu-Cuypers CP, Kagemann L, Cuilla TA, Kreigelstein G,. "Atlas of Ocular Blood Flow: Vascular Anatomy, Pathophysiology, and Metabolism," Butterworth, Philadelphia, PA, 2010, pp. 1-119.
Jia Y, Bailey ST, Hwang TS, McClintic SM, Gao SS, Pennesi ME, Flaxel CJ, Lauer AK, Wilson DJ, Hornegger J, Fujimoto JG, Huang D, "Quantitative optical coherence tomography angiography of vascular abnormalities in the living human eye," Proc Natl Acad Sci May 5, 2015;112(18):E2395-40.
Lutty GA, "Effects of diabetes on the eye," IOVS Dec. 2013;54(14):81-87.
Bhutto I, Lutty GA, "Understanding age-related macular degeneration (AMD): Relationships between the photoreceptor/retinal pigment epithelium/Bruch's membrane/choriocapillaris complex," Mol Aspects Med. Aug. 2012; 33(4): 295-317.
Mcleod DS, Grebe R, Bhutto I, Merges C, Baba T, Lutty GA, "Relationship between RPE and choriocapillaris in age-related macular degeneration," Invest Ophthalmol Vis Sci 2009;50:4982-4991.
Flammer J, Orgül S, Costa VP, Orzalesi N, Kriegelstein GK, Serra LM, Renard J-P, Stefánsson E, "The impact of ocular blood flow in glaucoma," Prog Ret Res 2002;21:359-393.
Grunwald JE, Piltz J, Hariprasad SM, DuPont J, "Optic Nerve and Choroidal Circulation in Glaucoma," Invest Ophthalmol Vis Sci, 1998; 39: No. 12:2329-2336.
Grieshaber MD, Flammer F, "Blood flow in glaucoma," Curr Opin Ophthalmol, 2005;16:79-83.
Marangoni D, Falsini B, Colotto A, Salgarello T, Anselmi G, Fadda A, DiRenzo AD, Campos EC, Riva CE, "Subfoveal choroidal blood flow and central retinal function in early glaucoma," Acta Ophthalmol. 2012: 90: e288-e294.
Cherecheneau AP, Garhofer G, Schmidl D, Werkmeister R, Schmetterer L, "Ocular perfusion pressure and ocular blood flow in glaucoma," Curr Opin Pharmacol 2013, 13;36-42.
Yang YC, Hulbert MFG, Batterbury M, Clearkin LG, "Pulsatile ocular blood flow measurements in healthy eyes: reproducibility and reference values," J Glaucoma 1997;6:175-179.
Harris A, et al. "Progress in Measurement of Ocular Blood Flow and Relevance to Our Understanding of Glaucoma and Age-Related Macular Degeneration," Progress in Retinal and Eye Research vol. 18, No. 5, pp. 669 to 687, 1999.

(56) References Cited

OTHER PUBLICATIONS

Krakau C.E.T., "Calculation of the Pulsatile Ocular Blood Flow," Investigative Ophthalmology & Visual Science, vol. 33, No. 9, Aug. 1992, pp. 2754-2756.

Silver, David et al. "Estimation of pulsatile ocular blood flow from intraocular pressure," abstract of article appearing at Acta Ophthalmologica, vol. 67, Issue S191, pp. 25-29, Mar. 1989.

Chang, BYP et al., "Local anaesthetic techniques and pulsatile ocular blood flow," Br J Ophthalmol 2000 84: 1260-1263.

Savage, H.I. et al., "Differences in Pulsatile Ocular Blood Flow among Three Classifications of Diabetic Retinopathy," Investigative Ophthalmology & Visual Science, Dec. 2004, vol. 45, 4504-4509.

Jain, MR, "A clinical evaluation of the applanation pneumatonograph," Brit. J. Ophthal. (1976) 6o, 107.

Durham, DG, et al., "Pneumatic Applanation Tonometer," Trans Am Ophthalmol Otolanyngol, Nov.-Dec. 1965 69(6) 1029-47.

Polska, E, et al., "Twelve hour reproducibility of choroidal blood flow parameters in healthy subjects," Br J Ophthalmol 2004;88:533-537.

Bayerle-Eder, M, et al., "Effect of a nifedipine induced reduction in blood pressure on the association between ocular pulse amplitude and ocular fundus pulsation amplitude in systemic hypertension," Br J Ophthalmol 2005;89:704-708.

Schmetterer et al., "A comparison between laser interferometric measurement of fundus pulsation and pneumotonometric measurement of pulsatile ocular blood flow, 2. Effects of changes in pCO2 and pO2 and of soproterenol," Eye (2000) 14, 46-52.

Wikipedia, "Brushless DC Electric Motor," Jun. 13, 2016, pp. 1-10, https://en.wikipedia.org/w/index.php?title=Brushless_DC_electric_motor&oldid=704641135.

Wikipedia, "Orifice plate," Oct. 4, 2017, pp. 1-6, https://en.wikipedia.org/wiki/Orifice_plate.

Wikipedia, "Venturi effect," Sep. 12, 2017, pp. 1-5, https://en.wikipedia.org/wiki/Venturi_effect.

Durham, et al., "Pneumatic Applanation Tonometer," Transactions American Academy of Ophthalmology and Otolaryngology, vol. 69, No. 6, Nov. 1, 1965, pp. 1029-1047.

International Search Report, European Patent Office, International Application No. PCT/US2017/019250, Jul. 6, 2017, pp. 1-16.

OA Japan 2018-543617, DuBois et al., Office Action pp. 1-6.

Claims in JP2018-543617, DuBois et al., Claims 1-15.

\* cited by examiner

```
Mean IOP              (mmHg): 27.9
Pulse Rate            (1/min): 69.4
Pulsatile Amplitude   (mmHg): 2.56

Net Pulsatile Flow        (uL/s): 3.73
Net Pulsatile Flow        (uL/m): 194.0
Peak Net Pulsatile Flow   (uL/s): 7.1
Peak Net Pulsatile Flow   (uL/m): 425.3
```

FIGURE 12

COMPOSITE OCULAR BLOOD FLOW ANALYZER

A portion of the disclosure of this patent document contains material subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

This disclosure relates to ophthalmology, and in particular, to the analysis of ocular blood flow and other workings of the human body. More specifically, this disclosure relates to a novel system that produces accurate, stable, and repeatable low distortion measurements of intraocular pressure (IOP) as a function of time from which reliable data about ocular blood flow (OBF) can be derived. A health care provider can assess the ocular blood flow data in conjunction with appropriate clinical correlation, such as additional tests, observations, and historical patient information, to detect abnormalities and diseases in the eye and other parts of the body. For example, a health care provider can detect glaucoma, carotid occlusive disease, and cerebral vascular disease. Also, a health care provider can detect changes in ocular blood flow and can provide appropriate therapeutic interventions such as pharmaceuticals and surgery.

This disclosure relates to a method and apparatus for use in accurately measuring and recording minute and rapid fluid pressure fluctuations within a closed, fluid filled elastic chamber such as the eye. The variation in intraocular pressure occurs in response to each cardiac cycle that generates a bolus of blood that enters the eye and later drains from the eye. From the rapid, accurate, and continuous recording of the variation in intraocular pressure made possible by the subject matter of this disclosure, various diagnostic information, including but not limited to, intraocular pressure pulse amplitudes, pulsatile ocular blood flow, pulsatile ocular blood volume, and equivalent Gosling pulsatility index may be ascertained.

BACKGROUND

A tonometer is a device used by eye care providers to measure the fluid pressure inside the eye, commonly referred to as the intraocular pressure or IOP. The most common device for measuring IOP is the applanation tonometer, which directs a controlled force against the cornea to flatten or applanate the cornea. The IOP opposes and balances the applied force. When a predetermined area of the cornea has been applanated, the applied force is considered to be equal to the IOP and can be recorded as such. The alleged gold standard in applanation tonometers is the Goldman tonometer [Whitacre, 1993] used in almost all eye examinations. The Goldman tonometer and other applanation tonometers, however, are limited in that they only supply a static IOP result averaged over time, whereas the device disclosed and claimed in this document reveals a time-resolved IOP. The prior applanation tonometers also do not provide any indication of ocular blood flow.

Efforts have been made to ascertain OBF from the IOP data returned by pneumatic applanation tonometers (Langham, 1989), in which the force applied to the eye is created by a flow of air or other gas directed to a probe that is placed in contact with the eye, but the results have been unsatisfactory because the readings of IOP from these instruments are inaccurate, unstable, and not repeatable. See, for example, the Langham Ocular and Cerebral Vasculometer, the OBF system, the Paradigm Ocular Blood Flow Analyzer, and the Tonoplus™ with Blood Flow instruments [Oppenheim, 1993; Spraul, 1998], which are no longer on the market.

Pneumatic ocular pressure probes measure and record variations in intraocular pressure over time. The literature gives a full description and theoretical analysis of the operating principles of the pneumatic ocular pressure probe (Langham, 1968) and an analysis of its ability to accurately and rapidly measure and record variations in intraocular pressure over time (Walker and Langham, 1975, Walker et al. 1975, Walker & Litovitz 1972).

Ocular pressure is a reflection of blood flowing into the eye. Ocular blood flowing into the eye comes from the internal carotid artery, which arises directly from the heart. The ophthalmic artery is the first branch off the carotid artery in the cranium. The second branches from the carotid artery become the major arteries feeding the brain. Perturbations such as internal carotid artery stenosis can be seen in the measurement of ocular blood flow entering the eye via the internal carotid and ophthalmic arteries (Langham, 2009).

Ocular blood flow within the eye arises from the ophthalmic artery. The ophthalmic artery gives off nine posterior ciliary arteries to supply the optic nerve and a vast rich plexus of blood vessels comprising the choroid, which nourishes the outer layers of the retina and pigment layer of the eye. The ophthalmic artery also gives rise to a single central retinal artery whose branches nourish the inner retina of the eye.

There are two general categories of devices that measure ocular blood flow parameters: (1) those that derive blood flow from the expansion of a globe filled with an incompressible fluid and (2) those that are optically based devices that have advanced from the widely used Ocular Computerized Tomography (OCT) platform or Scanning Laser Ophthalmoscope (SLO) technologies combined with Doppler techniques, retinal vessel analysis, and erythrocyte tracking.

Pulsatile ocular blood flow (POBF) is due to the bolus of blood entering the eye with each beat of the heart. Because 90% of the ocular blood flow is derived from the choroidal circulation, the POBF is generally accepted as equivalent to the choroidal circulation (Zion, 2007). There are two ways to measure POBF: (1) at the surface of the eye based on the established pressure-volume relation of the eye and (2) measurement of the fundus pulsation amplitude using laser interferometry. The validity of the transformation of the oscillatory waveform of intraocular pressure to pulsatile ocular blood flow and pulsatile ocular blood volume based on the pressure-volume relation is described in the literature (Eisenlohr, 1962; Silver and Farrell, 1994; Silver and Geyer, 2000). The measurement of choroidal blood flow based on fundus pulsation amplitude using laser interferometry is also accepted as a measure of choroidal or composite blood flow (Schmetterer, 2000, Berisha 2010). Only POBF measured at the surface of the eye is independent of the need for a clear ocular media, however.

Measurement of choroidal blood flow is difficult in optical based technologies because the pigmented layer of the eye prevents visualization of the choroid except in the absolute center of the retina or the macula. This visualized area comprises only about 5.5 square mm of the entire area of the retina and choroid, which measures about 1094 square mm in total (Schmetter, 2012 and Harris 2010).

Newer optical based technologies such as swept source ocular computerized tomography and ocular computerized tomographic angiography (Jia, 2015) are now in development stages. These have the potential to measure larger areas of the choroid but are expensive to produce and develop. In addition, all optical based technologies are dependent on clear ocular media from the front of the eye or the cornea through the lens to the back of the eye where the retina and the optic nerve transmit visual information to the brain. Thus, common conditions such as cataracts may alter the measurement of ocular blood flow within the eye using optical based technologies. As a result, these technologies are not as accurate in many of the elderly patients who may have comorbid eye conditions such as cataracts.

Measurement of retinal blood flow is primarily accomplished through optical based technologies (Schmetter 2012, Harris, 2010). Most of these techniques focus on the measurement of retinal blood flow (only 10% of ocular blood flow) because they are based on the use of the retinal vessel analyzer which cannot detect choroidal vessels and in most devices only measures a small segment of a retinal vessel, about 50 to 150 um. Statistical quantification techniques will increase the validity of these measurements as they are developed.

Perturbations of ocular blood flow to and within the eye are described in the scientific literature as a major contributor to the pathogenesis of multiple blinding conditions, for example, diabetic retinopathy, glaucoma, and age related macular degeneration. Others include ischemic optic neuropathy, retinal venous occlusive disease, and retinopathy of prematurity. In addition to ophthalmic conditions, changes in ocular blood flow have also been identified in systemic conditions such as Alzheimer's and carotid occlusive disease (Langham, 2009).

The majority of the scientific literature regarding the measure of perturbations of ocular blood flow has been based on studies of the retinal circulation, which represents only 10-15% of the ocular blood flow. However the choroidal circulation represents 85-90% of ocular blood flow. Only recently has the importance of the choroidal circulation been recognized as contributing to the early development of diabetic retinopathy (Lutty, 2013), aging macular degeneration (Bhutto, 2012, McLeod 2009), and glaucoma (Flammer 2002, Grunwald 1998, Grieshaber 2005, Marangoni 2012, and Cherecheanu 2012). Methods providing rapid and accurate measurement of the choroidal circulation are essential to early diagnosis of these blinding conditions so that preventative therapies that may slow progression of the conditions can be employed.

There are a number of factors that can influence the measurement of POBF. The literature describes POBF values that are generally higher in males than in females in addition to an overlapping range of normal and abnormal values in glaucoma and other diseases (Yang, 1997). POBF is influenced by refractive error, axial length of the eye, central corneal thickness, age, sex, and ethnic origin (Zion, 2007). Because of variations between individuals, the technique is characterized by limited reproducibility (Spraul, 1998; Yang, 1997). These variations would make statistical evaluation of sensitivity and specificity using POBF as an indicator of a particular disease difficult. However, the high level of accuracy, reproducibility and repeatability of POBF measurements in individual patients is key to its clinical value. In this regard, the ability to measure changes in POBF with application of topical and systemic medications and to measure the change in POBF in individual patients over time are valuable indicators to clinicians providing eye care to their patients.

There has been a long-felt, but unfulfilled, need well established in the literature for the transformation of the oscillatory waveform of intraocular pressure to rapid and accurate continuous measurement and recording of the variation in intraocular pressure, intraocular pressure pulse amplitudes, pulsatile ocular blood flow, pulsatile ocular blood volume, equivalent Gosling pulsatility index, and other aspects of ocular blood flow (Silver and Farrell, 1994; Silver and Geyer, 2000). In addition, many peer-reviewed articles exist in the international literature demonstrating the connection between the nature of pulsatile ocular blood flow indices and many eye diseases and conditions. Analysis of this literature, however, points to factors known to make difficult the measurement of the pulsatile ocular blood flow and pulsatile ocular blood volume. Those factors include sex, the corneal thickness (especially after corneal refractive surgery or cornea crosslinking procedures), the size of the globe as measured by refraction or axial length, hysteresis, elasticity, and ocular or scleral rigidity. Therefore, accurate measurement of pulsatile ocular blood flow is crucial to the successful assessment and treatment of abnormal conditions in the eye and other areas in the human body, but suitable measurement equipment currently is unavailable.

Prior pneumatics based instruments were engineered with restrictions on the flow rate and pressure of air or gas to the probe that is compatible with the internal pressure of the eye to ensure safe operation over the range of 10 to 40 mmHg IOP. For example, the FDA approved Paradigm instrument produced a pressure at the eye/membrane interface of 50 mmHg in response to an IOP of 10 mmHg. An instrument in accordance with this invention at all times delivers significantly lower pressures relative to IOP.

The challenge previous engineers faced was to ensure sufficient flow to cause a rapid and large change in pressure in the probe and measurement system as the eye/membrane interface varied in response to changes in IOP caused by inflow and outflow of blood circulation per heartbeat. All found this to be the significant barrier to success in exposing the measuring devices to enough displacement to measure, while remaining within the constraints imposed by non-interference with the IOP caused by pressure from the probe itself. The figure given above of 50 mmHg probe pressure to 10 mmHg IOP is typical of previous instruments.

Several attempts were made to provide enough flow over time to yield distinct, rapid, and sufficiently large changes in probe pressure in response to the changes in IOP as a result of blood circulation in the eye. Overall, there were no significant differences between instruments, and the net result is best described by the representatives of each predicate instrument manufacturer, who stated "we could never get it to work." The basics in all instruments include an air source capable of producing many times the pressure actually needed. This in all cases was either a diaphragm or piston pump that produced with a significant output oscillation component. The reason for the excessive pressure at the initial air source is to divide the oscillations of the pump over time to produce as little noise as possible in the air source. This excess of pressure had to be dealt with before exposure to the eye. The air supply was also far too noisy, the noise at this point in these systems was far in excess of signal amplitude to be measured. Thus, a first component added after the pump in all systems was a pneumatic pressure regulator. Pressure regulators deliver a constant pressure differential across an entry and exit port. However, they limit the flow in so doing. As it turns out a pressure regulator at best produces a marginally useful envelope of flow over time when set to pressure that is safe for operation of the instrument tip. A thin stream of air also yielded a dynamic whereby the probe is hyper sensitive to the environmental variables present at the eye surface, causing difficulty in achieving a measurable condition quickly and maintaining the position for the duration of the measurement.

Airflow in large enough volume over time is critical to proper operation of electronic measurement of pressure changes resulting from variations in flow. The second component used downstream from the pressure regulator was a needle valve arrangement to create a backpressure against the inflow of disturbed air from the regulator outlet. This smooths noise that was still unacceptably high in the airflow but further restricts the useful flow of gas or air needed to produce a rapid and reliable change in pressure in the probe in response to change in IOP over time. Also, by this time the inflow of air to the tip was constrained to the point where repeatable measurements taken with tips, even taken from the same manufacturing lot, resulted in different measurements of the same eye under the same conditions due to the minute variations in manufacture being sufficient relative to the small air flow to alter the tip to eye interface dynamics. This same weakness is evident in variations between operations of different probes due to minute wear and manufacturing variations. Airflow in large enough volume, while still operating in the established safe pressure range, without allowing too much noise, was the primary challenge engineers sought to solve.

A third type of device was employed to meet this challenge, this being a chamber or plenum in the airstream just prior to the probe. This was in attempt to filter or smooth noise in the airstream. This particular instrument suppresses the measured waveforms while allowing easier and more repeatable measurements. The best results observed in old machines either suppress the signal being measured, or create non-repeatability and non-linearity of measurements.

BIBLIOGRAPHY

1. Whitacre M, Stein R. Sources of error with use of Goldmann-type tonometers. Surv Ophthalmol 1993; 38(1):1-30
2. Langham M E, Farrell R A, O'Brien V O, Silver D M, Schilder P. Blood flow in the human eye. Acta Ophthalmologica 1989: 191(Suppl):9-13.
3. Oppenheim B, Dickersin K, Min Y I, Schockett S (1993) Reliability of measurements using the Langham ocular blood flow system. Invest Ophthalmol Vis Sci 1993: 34 [Suppl]:940.
4. Spraul C, Lang G E, Ronzani M, Hogel J, Lang G K. Reproducibility of measurements with a new slit lamp mounted ocular blood flow tonograph. Graefe's Arch Clin Exp Ophthalmol 1998; 236:274-279.
5. Langham M E, McCarthy, E, A rapid pneumatic applanation tonometer: Comparative findings and evaluation. Arch Ophthalmol 1968; 79; 389-399.
6. Walker R E, M E. Pneumatic applanation tonometer studies. III. Analysis of the floating tip sensor. Exp Eye Res 1975; 20:167-172.
7. Walker R E, Compton G A, Langham, M E. Pneumatic applanation tonometer studies. IV. Analysis of pulsatile response. Exp Eye Res 1975; 20:245-253
8. Walker R E, Litovitz T L. Pneumatic applanation tonometer studies. II. Rabbit cornea data. Exp Eye Res 1972; 13:187-193.
9. Langham M E. *Ischemia and Loss of Vascular Autoregulation in Ocular and Cerebral Disease: A New Perspective*. Springer Science+Business Media, LLC, New York, NY, 2009.
10. Zion I B, Harris A, Siesky B, Shulman S, McCranor, Garzozi H J. Pulsatile ocular blood flow: relationship with flow velocities in vessels supplying the retina and choroid. Br J Ophthalmol 2007; 91:882-884.
11. Eisenlohr J E, Langham M E, Maumenee A E. Manometric studies of the pressure-volume relationship in living and enucleated eyes of individual human subjects. Br J Ophthalmol 1962; 46:536-548.
12. Silver D M, Farrell R A. (1994). Validity of pulsatile ocular blood flow measurements. Surv Ophthalmol 1994; 38:572-580.
13. Silver D M, Geyer O. Pressure-volume relation for the living human eye. Curr Eye Res 2000; 20(2):115-120.
14. Schmetterer L, Dallinger S, Findl O, Eichler H-G, Wolzt M. A comparison between laser interferometric measurement of fundus pulsation and pneumotonometric measurement of pulsatile ocular blood flow. Eye 2000; 14:39-45.
15. Berisha F, Findl O, Last M, Kiss B, Schmetterer L. A study comparing ocular pressure pulse and ocular fundus pulse in dependence of axial length and ocular volume. Acta Ophthalmoligica 2010; 88:766-772.
16. Schmetterer L, Kiel J W (editors). *Ocular Blood Flow*. Springer-Verlag Berlin Heidelberg, Heidelberg New York Dordrecht London, 2012.
17. Harris A, Jonescu-Cuypers C P, Kagemann L, Cuilla T A, Kreigelstein G K. *Atlas of Ocular Blood Flow: Vascular Anatomy, Pathophysiology, and Metabolism*. Butterworth, 2010
18. Jia Y, Bailey S T, Hwang T S, McClintic S M, Gao S S, Pennesi M E, Flaxel C J, Lauer A K, Wilson D J, Hornegger J, Fujimoto J G, Huang D. Quantitative optical coherence tomography angiography of vascular abnormalities in the living human eye. Proc Natl Acad Sci 2015 May 5; 112(18):E2395-40
19. Lutty G A. Effects of diabetes on the eye. IOVS 2013 December; 54(14):81-87.
20. Bhutto I, Lutty G A. Understanding age-related macular degeneration (AMD): Relationships between the photoreceptor/retinal pigment epithelium/Bruch's membrane/choriocapillaris complex. Mol Aspects Med. 2012 August; 33(4): 295-317.
21. McLeod D S, Grebe R, Bhutto I, Merges C, Baba T, Lutty G A. Relationship between RPE and choriocapillaris in age-related macular degeneration. Invest Ophthalmol Vis Sci 2009; 50:4982-4991.
22. Flammer J, Orgul S, Costa V P, Orzalesi N, Kriegelstein G K, Serra L M, Renard J-P, Stefánsson E. The impact of ocular blood flow in glaucoma. Prog Ret Res 2002; 21:359-393.
23. Grunwald J E, Piltz J, Hariprasad S M, DuPont J. Optic Nerve and Choroidal Circulation in Glaucoma. Invest Ophthalmol Vis Sci, 1998; 39: No. 12:2329-2336.
24. Grieshaber M D, Flammer F. Blood flow in glaucoma. Curr Opin Ophthalmol, 2005; 16:79-83.
25. Marangoni D, Falsini B, Colotto A, Salgarello T, Anselmi G, Fadda A, DiRenzo A D, Campos E C, Riva C E. Subfoveal choroidal blood flow and central retinal function in early glaucoma. Acta Ophthalmol. 2012: 90: e288-e294

26. Cherecheanu A P, Garhofer G, Schmidl D, Werkmeister R, Schmetterer L. Ocular perfusion pressure and ocular blood flow in glaucoma. Curr Opin Pharmacol 2013, 13; 36-42.
27. Yang Y C, Hulbert M F G, Batterbury M, Clearkin L G. Pulsatile ocular blood flow measurements in healthy eyes: reproducibility and reference values. *J Glaucoma* 1997; 6:175-179.
28. Armaly M F. On the distribution of applanation pressure. I. Statistical features and the effect of age, sex, and family history of glaucoma. *Arch Ophthalmol* 1965: 73:11-18.

SUMMARY

In one embodiment, the inventors of the subject matter of this disclosure have solved the problems of prior ocular blood flow analyzers by developing a novel air delivery system in combination with a pressure probe that can produce accurate, linear, and noise-free readings of intraocular pressure, which permits the production of accurate and repeatable data about ocular blood flow, particularly composite ocular blood flow, and more particularly, composite pulsatile ocular blood flow, which includes both retinal and choroidal components of the pulsatile ocular blood flow. The inventors also have developed novel electronic circuitry that quickly acquires and processes raw pressure data from the probe and produces data about IOP and ocular blood flow with an accuracy and precision significantly beyond that which has been available to date. The accurate IOP and pulsatile ocular blood flow data produced by the invention increases the practitioner's ability to detect and assess over time abnormalities in the eye and other parts of the body.

The primary physical differences in the air supply of an instrument in accordance with one embodiment of the invention are in the use of different types of devices both at the pump and in place of the pressure regulator formerly used. First, the pump is a powerful brushless DC motor driven device, allowing high-speed operation with relatively smooth outflow of air. This type of motor is novel in that it maintains high torque so it does not tend to respond to increased resistance by slowing pump speed, pressure or volume. A constant supply of low noise pneumatic fluid at reliable pressure and flow is achieved.

Like its predecessors, the air from the new pump arrangement is at a higher flow and pressure than fits within the safe operation envelope already established for the instrument/eye interface. This is solved with the use of a pressure compensated flow regulator device that can be purely mechanically operated. The pressure compensated flow regulator is also available as an electronic version, which can also be used. The principle of a flow regulator is opposite to a pressure regulator in that this device attempts to maintain a constant volumetric flow over time versus a constant pressure over time at the cost of flow. At the same time, it acts (as does a pressure regulator) as a noise filter, reducing the threshold of noise from the pump below the signal sought to be measured. The increased flow produced, accompanied by decreased pressure, has been demonstrated to operate stably as low as 20 mmHg probe pressure: 10 mmHg IOP, with a linear and proportional ascent over a range of IOP from 10 to 40 mmHg. Novel hardware here plays a significant role in reducing noise while maintaining enough energy in the fluid flow to permit detection of the IOP signal. A significantly higher margin of safety, accuracy, repeatability, and stability in use and responsiveness are shown by experimental results.

In detailed embodiments, a method and apparatus is involved for use in measuring and recording rapid and accurate fluid pressure within a closed organ without increasing the pressure within the organ itself. In particular, the system may measure the following indices, among others: (1) variation in intraocular pressure, (2) intraocular pressure pulse amplitudes, (3) pulsatile ocular blood flow, (4) pulsatile ocular blood volume, and (5) equivalent Gosling pulsatility index.

In one example of the invention, a pneumatic probe and tip in the measurement apparatus contains a thin walled tube which initially is in contact with a flexible membrane covering the distal end of the tube and is connected to a pneumatic pump which increases the gauge pressure in the probe. Probe pressure measurements may be made at a rate of at least 100 times per second over a period of about 10 to 15 seconds or more for the measurement of indices (1-5) above. The pressure measurements can be made at even higher rates such as 200 times per second or more. In specific examples of a blood flow measurement apparatus, a pump is connected to the probe with a soft plastic tube communicating with a pressure chamber encased in a probe handle. A pressure transducer communicates with the pressure chamber to measure probe pressure. The pressure changes measured by the pressure transducer are converted to electronic signals through a signal processor that creates an oscillating waveform representing the variation in intraocular pressure as a function of time. Illustratively, contact with the eye is at the ocular surface by means of a probe tip covered by a clean or sterile, single-use per patient, flexible membrane that separates the cornea from the pneumatic pressure inside the probe. The membrane transfers the pressure to the cornea. When the gauge pressure inside a tube pressing against the cornea exceeds the intraocular pressure by some amount, the inward directed force produced by the gauge pressure inside the probe overcomes the outward force induced by the intraocular pressure and cornea. At that pressure, a gap between the tube and the flexible membrane forms, releasing fluid from the tube, stabilizing the probe pressure, and feeding the internal probe pressure back through a second soft plastic tube to the pressure transducer. Alternatively, the pressure transducer may be integral with the probe housing rather than connected to the pressure chamber by a flexible tube.

The observed oscillations in intraocular pressure occur at the surface of the eye as a result of accommodating changes in the intraocular blood volume induced by the bolus of arterial blood created by each cardiac cycle. The oscillations are recorded by a pressure-sensing device or pressure transducer. Analogue electrical signals representing continuously varying probe pressure changes are produced and processed. The pulsatile ocular blood flow is derived from the continuous oscillatory pressure measurements acquired from the probe using predetermined relationships that link probe pressure to intraocular pressure, ocular volume change, and ocular volume flow.

BRIEF DESCRIPTION OF THE DRAWINGS

FIG. 12 is an example of numerically presented illustrative ocular blood flow data produced by a machine in accordance with the invention.

DETAILED DESCRIPTION

Figure 1:
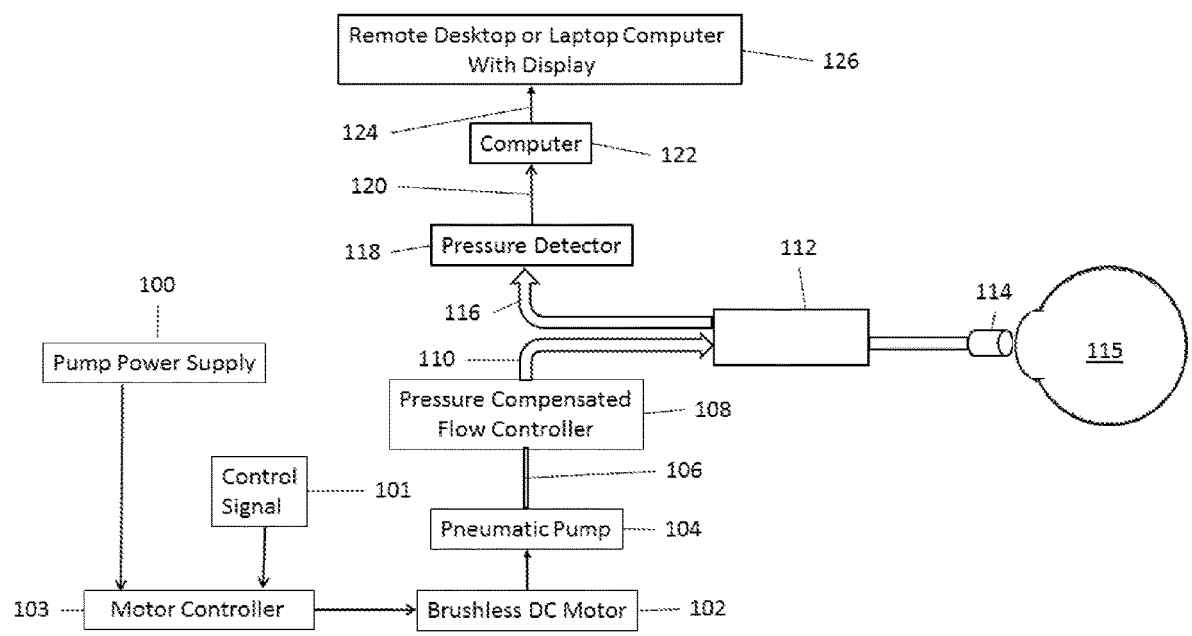
FIG. 1 is block diagram of the main components of an ocular blood flow analyzer constructed in accordance with the invention.

FIG. 1 shows an example of an ocular blood flow analyzer in accordance with the invention. The architecture of the OBF analyzer shown in FIG. 1 comprises a system of electrical, electronic, and pneumatic components that produce ocular blood flow data that is superior to that produced by past and current devices and systems that purport to provide such data about ocular blood flow (OBF).

The architecture shown in FIG. 1 includes a power supply 100 that delivers a variable and controlled amount of electrical power to a brushless DC motor 102. A motor controller 103 interposed between the power supply 100 and the motor 102 determines the amount of electrical power delivered to the motor 102. The amount of power delivered to the motor 102 by the motor controller 103 is determined by the magnitude of a control voltage produced by a control signal generator 101. The control signal generator 101 may be implemented as a manually set tap on a potentiometer connected to a dc voltage source. The voltage set by the position of the tap on the potentiometer constitutes a desired amount of power to be delivered by the motor controller 103 to the motor 102. Alternatively, the control signal generator 101 may be a computer that issues a voltage that constitutes a command to the motor controller 103 to deliver a predetermined amount of power to the motor 102. The computer may be the computer 122 described below or some other computer that controls the behavior of the motor 102 and the motor controller 103.

The motor 102 provides a constant controlled output torque to drive a pneumatic pump 104 that produces a supply of air or other pneumatic fluid at a predetermined controlled and relatively pulsation free pneumatic pressure to a fluid supply line 106, which may be a flexible hose or tube. This supply of fluid through the supply line 106 is directed to the input of a pressure compensated flow controller 108. The flow controller 108 provides a constant volumetric flow rate from its output regardless of pressure fluctuations. Illustratively, the flow controller 108 maintains a pneumatic fluid flow through the device of FIG. 1 at about 0-160 cc/sec. at pressures from about 20-60 mmHg. Also illustratively, the output 106 and the supply line 110 may be flexible hose or tubing that conveys pneumatic fluid from the pump 104 to the flow controller 108 and from the flow controller 108 to the probe 112, respectively.

The output of the flow controller 108 is directed on pneumatic supply line 110, which also may be a flexible hose or tube, to the input of a pneumatic tonometric probe 112. A probe tip 114 on the probe 112 is placed in contact with an eye 115 being measured. A pressure detect line 116 from the probe 112 has a series connected pressure detector 118, which produces a raw analog pressure signal representing the level of pressure in the probe 112. The pressure detector 118 may be connected to the probe 112 by way of a line 116, illustratively in the form of a flexible hose or conduit. Alternatively, the pressure detector 118 may directly mounted on the probe 112 so that it is in direct communication with the pressure chamber in the probe 112. Contact of the tip 114 of probe 112 with an eye 115 causes minute fluctuations in the raw probe pressure that are processed by the electronics of the OBF analyzer to produce accurate, stable, and repeatable low distortion IOP and OBF readings. By means of the arrangement so far described, the inventors have found that stable low pressures and constant airflows can be delivered to the probe 112, which improves the performance of the analyzer beyond that of prior instruments. This arrangement permits the accurate and drift free measurement of minute pressure variations resulting from the flow of blood to and from the eye 115 during each cardiac cycle.

The pressure compensated flow controller 108 may be any control system that establishes a desired substantially constant fluid flow rate toward the pressure probe 112 and initiates compensatory action to return the flow rate to the desired rate in response to deviations of the flow rate from the desired value, particularly in response to pressure fluctuations that cause deviations from the desired flow rate. Flow rate controller 108 may comprise a controllable restriction, such as a flow control valve in series with the pneumatic supply line 106 of the pump 104 and the pneumatic supply line 110 between the flow controller 108 and the probe 112. A basic flow control valve consists of a changeable aperture that opens to increase the flow rate or closes to slow the flow rate. Although any type of valve may be used, a needle valve that allows precision control of low fluid flow rates is preferred. These valves use an adjustable needle and valve stem to restrict or permit fluid flow. By controlling the amount that the needle valve obstructs the flow of fluid, that is, by opening or closing the needle valve by a certain amount, an operator can set the desired flow rate.

The flow rate through the flow control valve, such as the aforementioned needle valve, generally is related to the pressure drop across the valve. The higher the pressure drop across the valve, the greater the restriction in the flow path and thus the lower the output flow rate. The pressure compensated flow controller senses a change in the pressure drop across the flow control valve that causes a change in the flow rate through the valve. In response, the flow rate controller 108 initiates compensatory action to return the pressure drop, and the flow rate, to the desired value. A valve in series with the supply line 106 and modulated by changes in pressure drop across the needle valve may perform the compensatory action.

Figure 1A:
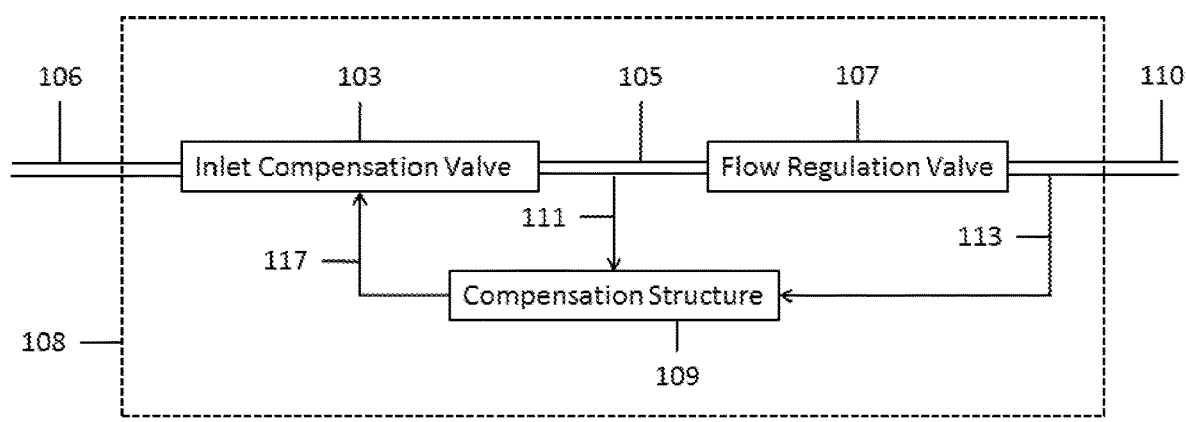
FIG. 1A is a schematic block diagram of the pressure compensated flow controller of FIG. 1.

FIG. 1A is a detailed block diagram of the pressure compensated flow controller 108 in FIG. 1 that specifically illustrates of the points described above. The flow controller 108 comprises an inlet compensation valve 103 in series with the supply line 106 from the pump 104. A fluid passage 105 connects the inlet compensation valve 103 to the input of a flow regulation valve 107, which preferably can be the needle valve described above. The output of the flow regulation valve 107 is connected to the supply line 110 that directs pneumatic fluid to the input of the probe 112. The flow regulation valve 107 creates a pressure drop from the input of the valve 107 to the output of the valve 107 that determines the rate of fluid flow to the probe 112. The pressure drop across the valve 107 is maintained at a constant value to keep the fluid flow rate to the probe 112 constant in the face of pressure fluctuations on either side of the valve 107. The degree to which the valve 107 is opened determines the magnitude of the pressure drop across the valve 107 and thus the desired fluid flow rate to the probe 112. Maintaining this pressure drop constant, and thereby maintaining the flow rate to the probe 112 constant, is accomplished by the operation of a compensation structure 109 connected to the input of the valve 107 by way of a fluid passage 111 and to the output of the valve 107 by way of a fluid passage 113. The fluid passage 111 conveys information to the compensation structure 109 about the magnitude of the upstream fluid pressure on the inlet side of the valve 107. Likewise, the fluid passage 113 conveys information to the compensation structure 109 about the magnitude of the downstream fluid pressure on the outlet side of the valve 107. The compensation structure 109 thus is responsive to the pressure drop across the valve 107. The compensation structure 109 has an output 117 that controls the opening of the input compensation valve 103. The compensation structure 109 is responsive to the pressure drop across the valve 107 by virtue of the fluid passages 111 and 113 and the output connection 117 to maintain the pressure drop across the valve 107 constant and thereby maintain the fluid flow rate to the probe 112 constant even though upstream or downstream fluid pressure may change. An example of a suitable pressure compensated constant flow rate valve and associated control structure is described in Beswick et al. U.S. Pat. No. 6,314,980.

Preferably, the selected pump 104 should produce an output as pulsation-free as possible. Completely pulse free airflow does not exist, especially not in the nano pressure levels being used here, but a suitable pump is a small diaphragm pump, which is less noisy than other alternatives in that such a diaphragm pump produces smaller, softened, output pulses. In addition, a brushless dc motor 102 drives the pump. Newer brushless dc motor technology produces an almost flat torque curve across rpm ranges. In this application, precise airflow is desirable as the pump bogs down less under variable loads. High or low rpm of the motor 102 both produce high torque. So the significance of the pump and motor is in providing a steady baseline pressure input to the flow control device. The fact that it is unresponsive to changes in load in the form of backpressure makes a big difference in repeatability of measuring conditions versus brushed motors and other technologies. Prior art instruments used a piston pump to overdrive the high-pressure side of the system to obtain a steady input by brute force. The older instruments then overcame noise by aggressive filtering that caused big problems in delivering an appropriate flow to the pressure probe 112.

In addition to exhibiting a flat speed-torque characteristic, brushless dc motors do not spark like brushed motors. Sparks generated by brushed motors are generally unacceptable in medical devices. Sparks could introduce noise and distortion into signals produced by electronic circuitry like that used in measurement apparatus disclosed here. Sparking could also damage delicate electronic circuitry of this OBF analyzer and could be dangerous to the patient and the operator of the instrument. It, therefore, is advantageous to use the brushless dc motor 102 to drive the pump 104.

The OBF analyzer of FIG. 1 also includes a computer 122 that rapidly performs data acquisition followed by digital signal processing that converts the raw pressure data from the probe 112 into IOP data and OBF data used by the practitioner to assess the health of a patient. Computer 122 first converts the analog raw probe pressure signal on line 120 from the pressure detector 118 into a stream of digital samples representing the raw probe pressure as a function of time that populates a data table in the computer 122. Alternatively, the analog raw pressure signal produced by the pressure detector 118 may be converted to a digital raw probe pressure signal samples by an analog to digital converter integral with the pressure detector 118. The digital samples created from the analog output of the pressure detector 118 populate a data table in the computer 122.

The computer 122 converts the digital raw probe pressure samples into digital samples representing measured IOP as a function of time. The computer 122 then converts the IOP data into OBF data. This OBF data may include one or more of the flow rate, flow volume, pulse amplitude, and pulse rate. The OBF data may also include pulsatility indices. The OBF data may be directed to a secure WiFi network 124 or any other secure network used by hospitals and healthcare institutions that is compliant with healthcare and medical laws and regulations such as the Health Insurance Portability and Accountability Act (HIPAA). The POBF data may be shown to an authorized user on a display connected to a laptop or desktop computer 126. The data may be displayed numerically or as waveforms of measurements as a function of time. In one embodiment of the invention, the computer 126 may be a Raspberry Pi running the Linux operating system illustratively programmed with suitable Python or IDL computer code compiled to binary code. The invention is not limited to implementations using the Raspberry Pi. Any computer able to be suitably programmed can be used, such as any suitably programmed Microsoft Windows based personal computer, Apple personal computer, or other computer.

Figure 2:
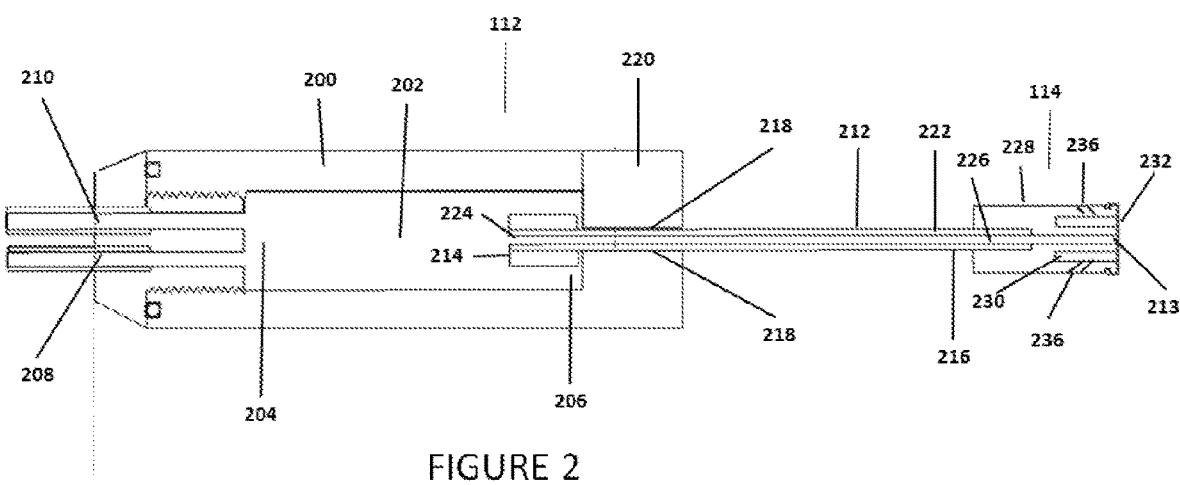
FIG. 2 is a schematic cross sectional diagram of the pressure probe shown in FIG. 1.

FIG. 2 shows a cross section of an example of the pressure probe 112 in FIG. 1. The probe 112 comprises a hollow elongated housing 200 defining a generally cylindrical pressure chamber 202. The pressure chamber 202 has proximal and distal ends 204 and 206 inside the housing 200. An inlet 208 into the housing 200 is adapted to admit air from the pump 104 and the flow rate controller 108 into the proximal end 204 of the pressure chamber 202. A port 210 in the housing 200 is adapted to communicate with the pressure sensor 118 that measures the air pressure in the chamber 202.

A shaft 212, having proximal and distal ends 214 and 216, extends from inside the pressure chamber 202 through the distal end 206 of the housing 200 to the exterior of the probe 112. The shaft 212 axially slides with respect to the housing 200 by way of a cylindrical bearing 218 defined between the outer surface of the shaft 212 and the inner surface of an opening in a distal end wall 220 of the housing 200 through which the shaft 212 extends.

An axially directed bore 222 is formed in the shaft 212. The bore 222 has proximal and distal ends 224 and 226, respectively. The bore 222 is in communication with the air in the pressure chamber 202 at its proximal end 224. A passage in the tip 228 attached to the distal end of the shaft 212 is coaxial with the bore 222 and forms a jet or nozzle 213 that directs air originating from the pump 104 toward the eye 115.

The tip 228 has a cylindrical venting chamber 230 into which nozzle 213 extends. A circular flexible membrane 232 covers the distal end of the nozzle 213 and the open end of the venting chamber 230 thus sealing the nozzle 213 and the venting chamber 230. Air flows from the pump 104 to the pressure chamber 202, and then through the bore 222 in the shaft 212 and the nozzle 213 toward the inner surface of the flexible membrane 232, which is placed in contact with an eye to measure IOP. Vents 236 exhaust air from the venting chamber 230 when the pressure from the pump 104 is sufficient to cause the membrane 232 to separate from the distal end of the jet 213.

In the steady state, the pump 104 directs pressurized pneumatic fluid to the input of the flow controller 108. The flow controller 108 outputs pneumatic fluid to the input port 208 of the probe 112 at a substantially constant volumetric flow rate. The pneumatic fluid flows into the pressure chamber 202, into the passage 222 in the rod 212, and then into the nozzle 213. The fluid coming out of the nozzle 213 applies a force against the inner surface of the membrane 232 forcing it away from the nozzle 213. This opens the nozzle 213 to the venting chamber 230 in the tip 114. Fluid can then flow into the venting chamber 230 and out of the instrument through the exhaust ports 236 in the tip 114.

The flow controller 108 maintains a substantially constant pressure drop across a flow restrictor inside the flow controller 108 to maintain a substantially constant rate of fluid flow to the probe 112. Pressure disturbances upstream or downstream of the flow controller 108 may change the pressure drop across the flow restrictor and thus may change the fluid flow rate to the probe. For example, when the probe tip 114 is placed against an eye for purposes of making a patient examination, the membrane 232 will pressed against the nozzle 213 closing the nozzle 213 from the venting chamber 230. This will increase the fluid pressure on the downstream side of the flow regulator, decrease the pressure drop across the flow restrictor, and decrease the fluid flow rate to the probe 112. Compensation structure in the flow controller 108 opposes the reduction in pressure drop and restores it to a desired value, which thus restores the flow rate to the desired value. The compensation structure may be a valve in the inlet of the flow controller 108 that opens to increase the pressure on the inlet side of the flow restrictor by admitting more fluid into the controller 108 to thereby increase the aforementioned pressure drop. A decrease in the fluid pressure on the downstream side of the controller 108 will result in compensation in the opposite direction to maintain a substantially constant desired flow rate to the probe 112. Pressure disturbances on the inlet side of the controller 108, such as pulsations from the pump 104, will result in similar compensatory action.

If tonometric pressure data is measured to a precision of about 0.05 mmHg or better, and at a cadence of at least 50 Hz (i.e. with a 20 ms sampling interval), then valuable clinical information may be obtained. Preferably, the sampling rate is at least 100 Hz or more, for example, 200 Hz and above. First, the device of FIGS. 1 and 2 obtains the raw probe input pressure from tee. From the tee, a new line (which is necessarily at the same pressure as the probe line) connects to a pressure measurement and digitization device 118. In concert with an embedded controller, the pressure data are repeatedly downloaded and logged. The data derived from the apparatus described above may be of very high quality (14 bit or higher pressure digitization at 100 Hz, or higher), exceeding the precision and temporal sampling requirements laid out above.

Signal processing code in the computer 122 automatically reads the data generated from the device and extracts a number of key parameters. More specifically, programs stored in the computer 122 sense the onset and the end of the pulsatile region of the pressure data, then extract the pulse rate, pulse amplitude, pulse volume, and the ocular blood flow. The algorithms also return the mean IOP.

The nozzle 213 at the end of the thin-walled tube 212 is initially in contact with the flexible membrane 232. The tube 212 is connected to a pneumatic pump 104 that increases the gauge pressure inside the pressure chamber 202. The membrane 232 transfers the pressure from the pump 104 to the cornea of the eye 115.

When the gauge pressure inside the tube 212 pressing against the cornea exceeds the IOP by some amount, the inward directed force produced by the air pressure overcomes the outward force induced by the IOP and is expressed by corneal deformation known as applanation. At that pressure, a gap between the tube 212 and the membrane 232 forms, releasing air from the tube 212 into venting chamber 230 and out of the probe 112 through the vents 236, and thereby stabilizing the probe pressure.

The outward pressure due to the IOP is spread over an area greater than the tube area because the cornea cannot abruptly deform at the edges of the tube. Because of additional factors such as air viscosity, the probe pressure is always greater than the IOP. There is, however, a relationship between the probe pressure and the IOP, which is unique for a given probe design at a given flow and pressure. This probe-IOP pressure relationship allows one to compute the IOP from the probe pressure. In the case of the disclosed device, the relationship is empirically observed to be linear, given by: PP=1.96(IOP)+1.75, where PP is the probe pressure and IOP is the eye pressure. Note that this relationship is partly a product of the probe design and should be determined empirically for each design. In the case of the prior art devices, there is no simple mathematical relationship, likely due to the lack of a flow controller. The invention is not limited to this specific relationship between probe pressure and intraocular pressure. The relationship should be a relationship observed empirically with the specific equipment being used to implement an ocular blood flow analyzer. This empirical observation can be made by comparing the pressure measured by the blood flow analyzer to a known pressure produced by any accurate mechanism that simulates the pressure of an actual eye, such as a water or air manometer, or other model eye. Measuring in vivo an actual eye having known pressure characteristics may also be used. Use of an illustrative water manometer to accomplish this task is described below. Another possibility for a manometer is a pulsatile air manometer that produces square wave pressure pulses.

When the probe is in contact with the eye, the probe pressure oscillates at an amplitude of around 6 to 10 mmHg and at a frequency equal to the pulse rate. The pulsatile ocular pressure oscillates at an amplitude of about 3 to 5 mmHg. See FIG. 4, which shows an example of raw pneumatic probe pressure data from an ocular blood flow analyzer in accordance with one example of the invention. See also FIG. 6, which shows an example of IOP derived from probe pressure data. Note in both cases the oscillatory signal impressed upon the overall pressure signal. The patient's pulse rate is about 77 beats per minute.

The tonometric probe pressure oscillates in response to ocular blood vessels cyclically swelling due the systolic/diastolic cycle. The process may be summarized as follows. As the ocular blood vessels swell, the ocular volume is increased. The increased ocular volume is resisted by the elasticity of the eye thereby increasing the IOP. This is analogous to a balloon being inflated. At larger volumes, the membrane is more tightly stretched and the internal pressure is higher.

A relationship exists between change in ocular pressure and change in ocular volume. Given the IOP-volume relationship, the IOP oscillations can be translated into changes in ocular volume. Since the fluid inside the eye is essentially incompressible, the change in volume must be due almost entirely in a normal eye to the change in vascular volume (ignoring the insignificant outflow component) and, therefore, must represent the net blood flow volume into the eye. In light of all this, the net pulsatile vascular flow can be computed.

Signal Processing Embodiment 1

Figure 3A:
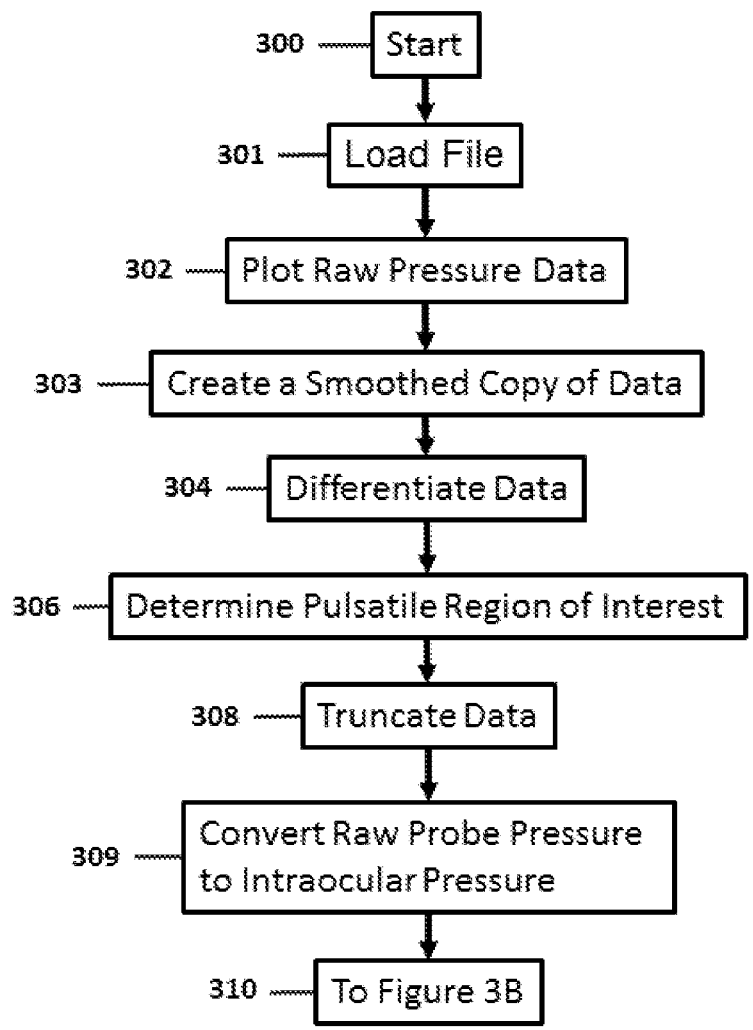
FIGS. 3A, 3B, and 3C are flow charts depicting the operation of one example of the software in the computer shown in FIG. 1.
Figure 3B:
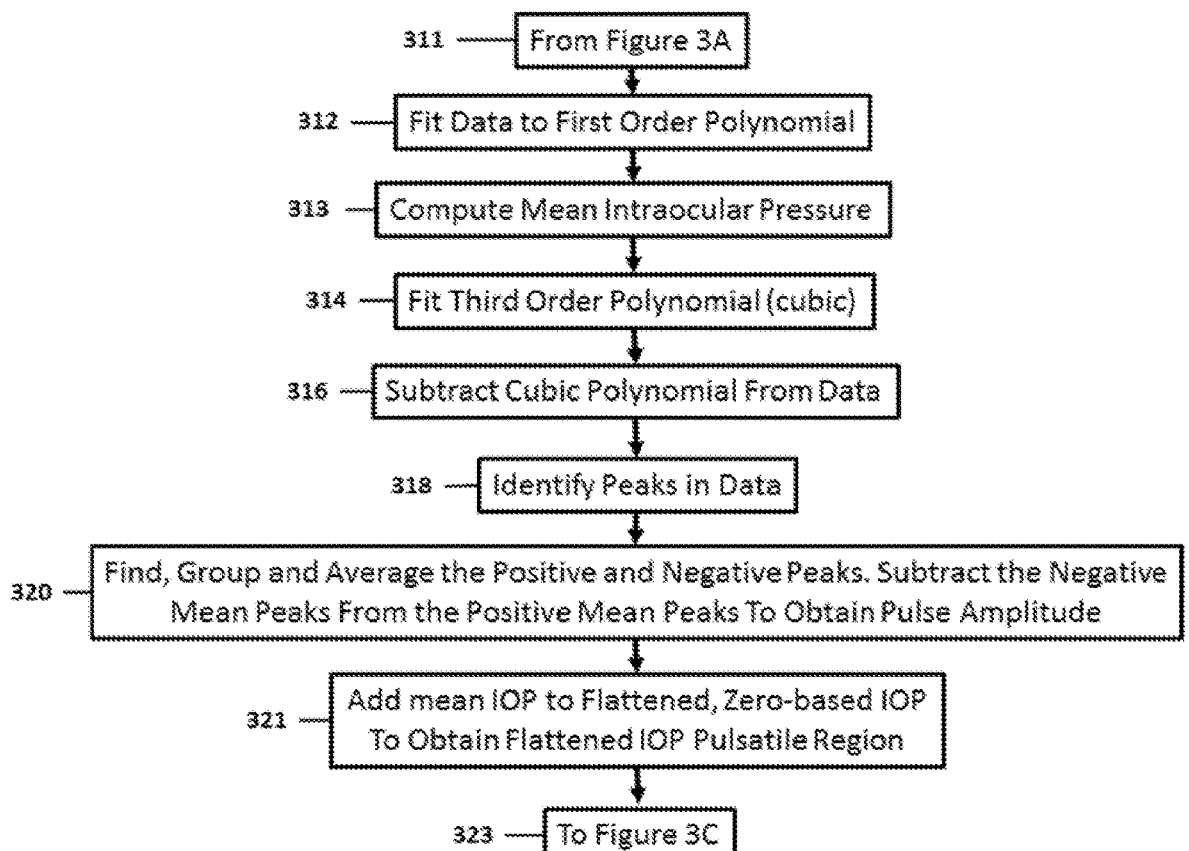
Figure 3C:
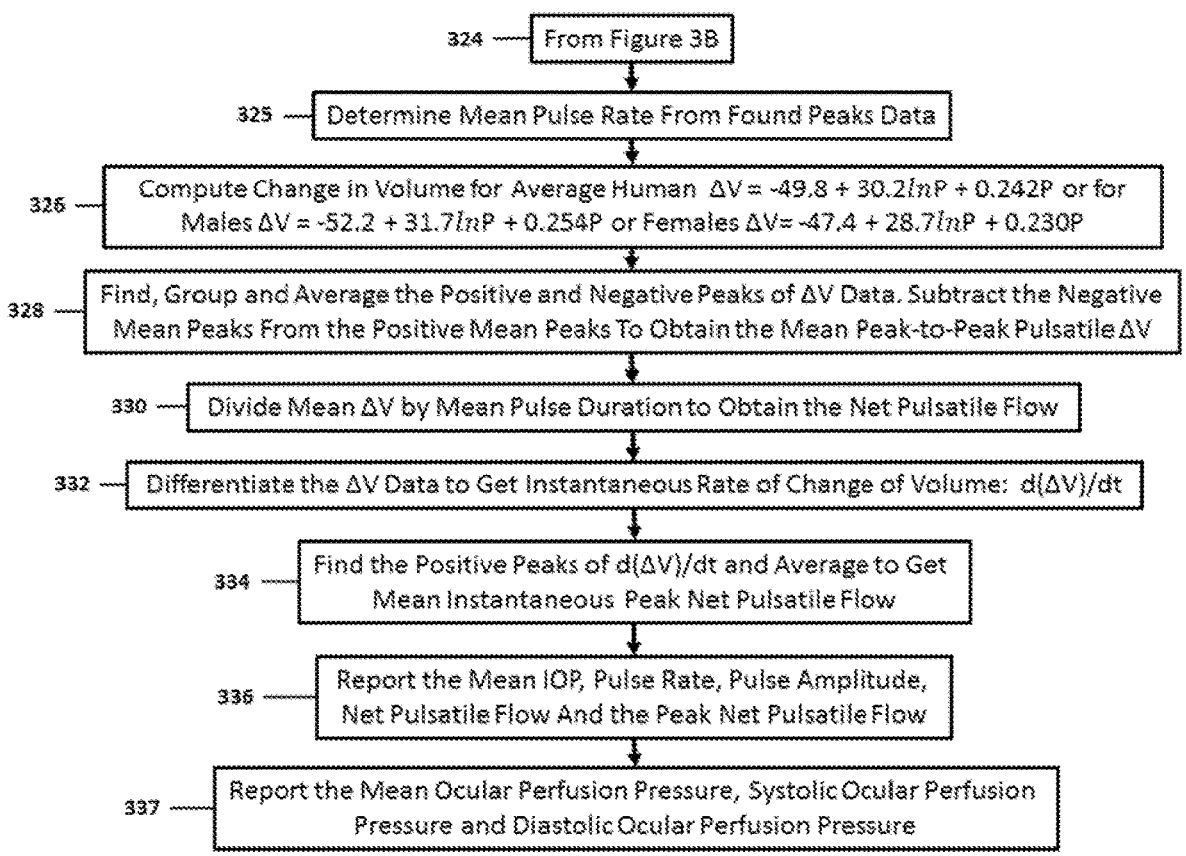
Figure 4:
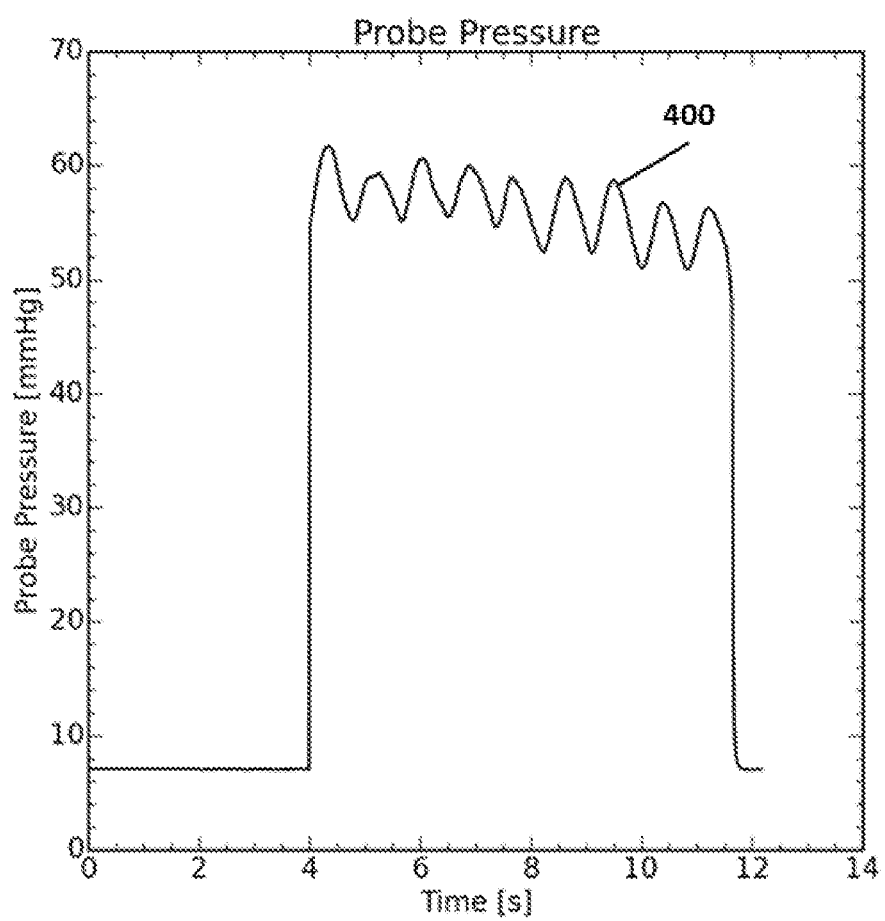
FIG. 4 is a plot of probe pressure versus time obtained as a result of an illustrative first eye examination.

FIGS. 3A, 3B, and 3C comprise a flow chart depicting in detail the operation of a first example of the software in the computer 122 that performs the signal processing part of this invention. The program begins in start block 300 in FIG. 3A. Next, in block 301, the program loads into memory a text file of raw pressure data collected from the probe 112. After loading the text file of data, the software, in block 302, creates a plot of the raw probe pressure data as a function of time 400, as shown in FIG. 4.

The data from the probe 112 contains a significant amount of noise that could adversely influence the measurement of intraocular pressure and blood flow. At least some of the noise can be removed without adversely influencing the pressure measurements by applying a judicious amount of smoothing to the noisy data. Accordingly, a smoothed copy of the data is created in block 303 in FIG. 3A. Illustratively, a boxcar filter or running mean filter is used to smooth the data. Such a filter maps each data point in a set of unsmoothed data to another data point in a set of smoothed data. For each data point in the unsmoothed data set, the boxcar filter averages the value of that data point with a predetermined number of other data points in the unsmoothed data set. That average then becomes one of the data points in the smoothed data set. For example, in the embodiment described here, a nine-element boxcar filter is used. The boxcar filter averages each pressure sample from the probe 112 with four of the immediately previous in time pressure samples from the probe 112 and four of the immediately next in time pressure samples from the probe 112. The average of these nine data points in the samples from the probe 112 then becomes a smoothed pressure sample in the smoothed data set. The degree of smoothing is tunable and is related to the length of the running mean (i.e. the length of the 'boxcar'). Although it is preferred that the boxcar filter described here be used to smooth the probe pressure data, other smoothing circuits or filters that can remove noise in the probe pressure data may be used instead.

There is usually some finesse required here, as one would ideally never have to use a smoothing filter in the first place. But, in the real world data is noisy. Smoothing helps to combat that noise, but at the obvious expense of also smoothing the signal. Typically, a person skilled in the art aims for a smoothing length that is greater than the typical coherence length of the noise, while significantly less than the smallest coherence length in the signal of interest. The coherence length of a signal is the period of that waveform. The coherence length of the noise may be the period of the lowest unwanted frequency component of the noise. The coherence length could also be the average, or some other mathematical function, of the periods of the noise frequencies. The smallest coherence length of interest in the signal is the period of the smallest frequency of interest, in this case, the pulse rate. The patient described above had a pulse rate of 77 beats per minute, or 1.28 beats per second. The period thus is 1/1.28 seconds or 780 milliseconds. The inventors have found that a suitable temporal width of the boxcar filter in this example of the invention is about 200 milliseconds, which is substantially smaller than the coherence length of the signal of interest. This translates into a boxcar temporal width of 9 or 11 consecutive samples when the sampling rate is 100 Hz. The coherence length of the noise is substantially below the 200 millisecond boxcar length, since good smoothing is obtained at this temporal boxcar width. To summarize, a person skilled in the art would select a boxcar length between the coherence length of the noise and the coherence length of the information content. This is what is done in the present code described here. Empirical testing and experience with the raw data and the desired signal data indicates what amount of smoothing is appropriate to remove noise without crushing the pressure signal.

Figure 5:
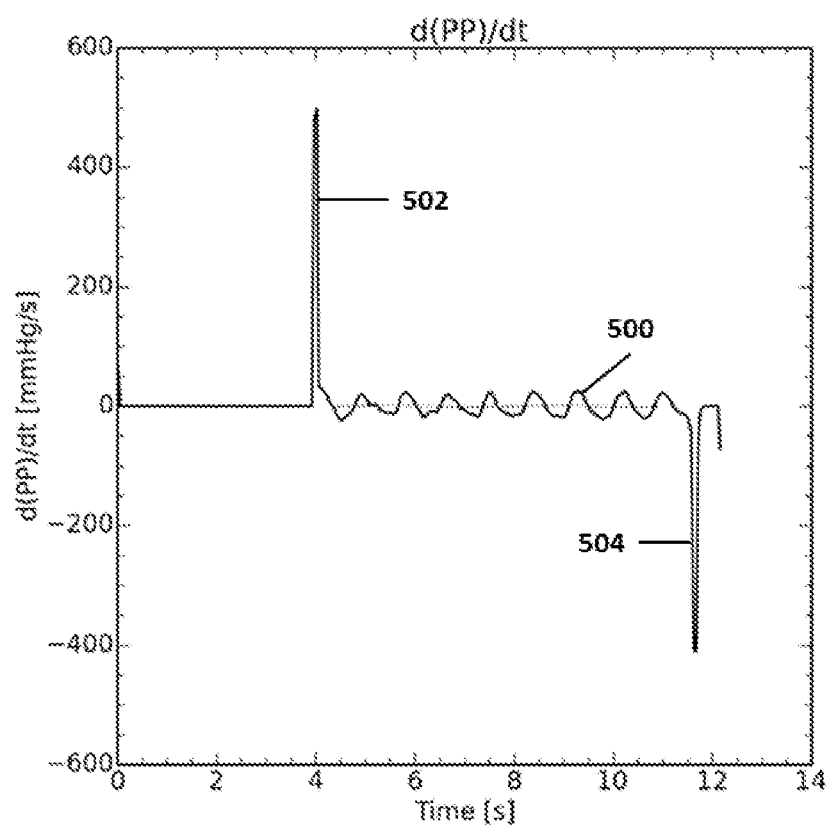
FIG. 5 is an illustrative plot of the derivative of probe pressure of FIG. 4 as a function of time.

Next, after smoothing the raw pressure data in block 303, the software automatically senses the onset and the end of the pulsatile regions of interest (ROI). This is done by differentiation of the smoothed input signal in block 304 in FIG. 3A. A differentiated signal is one that represents the local slope of the original signal. The slope of the pulsatile region never exceeds a certain value, but when the measurement begins, and when the measurement ends, there is a rather large slope change, positive at the beginning of the measurement interval, then negative at the end of the measurement interval, respectively. FIG. 5 shows the smoothed and differentiated raw probe pressure data 500. Regions of high values 502 and regions of low values 504 in the differentiated raw data correspond to regions of highly positive and highly negative slope, respectively, in the raw probe pressure data. Such regions only occur at the onset and termination of the measurement, in other words at the beginning and end of the region of interest.

These uniquely high slope regions may be sensed in block 306 in FIG. 3A by a thresholding method, giving the locations of the onset and end of the pulsatile region of interest (ROI). The software compares the values of the differentiated raw data and compares them to positive and negative thresholds. When the positive threshold is exceeded, the software has identified the start of the measurement. When the differentiated raw data is less than the negative threshold, the end of the measurement has been identified. The pulsatile region of interest is between the beginning and end of the measurement. The software then truncates the raw pressure data by contracting the found ROI by about one second, for example, in block 308, to be sure that the region being sampled truly represents the pulsatile region, and does not contain any excessive signal due simply to onset or termination pressure fluctuations.

Figure 6:
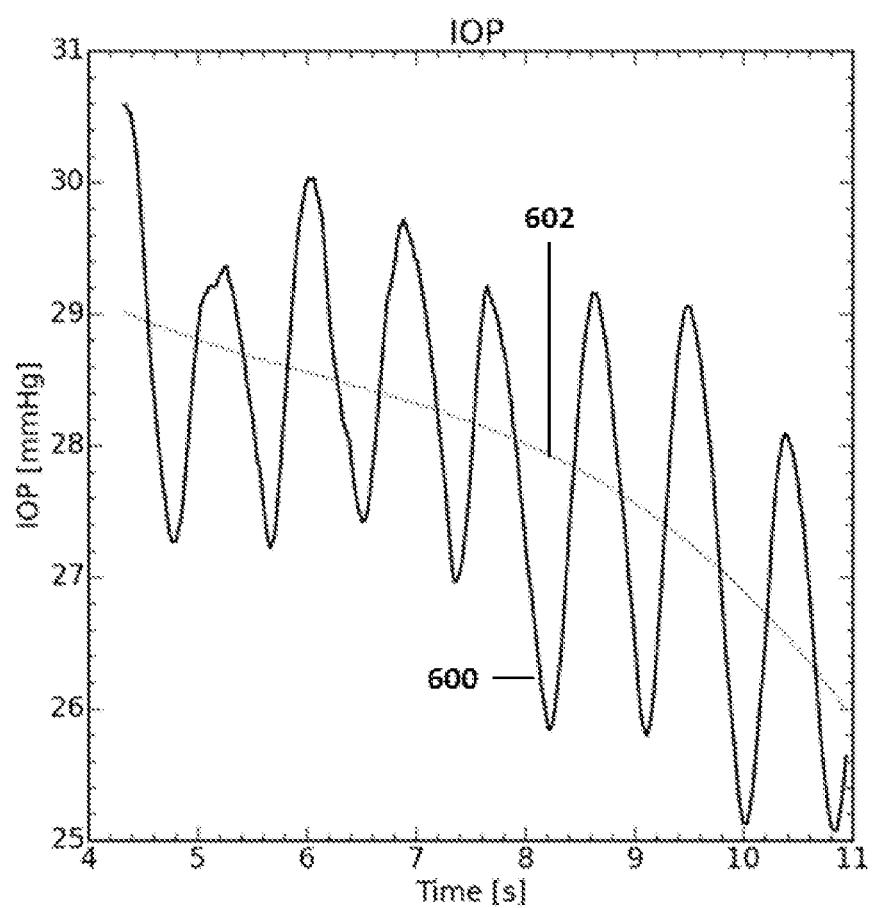
FIG. 6 is an illustrative plot of intraocular pressure as a function of time derived from the probe pressure data of FIG. 4 to which a third order polynomial has been fit.

Next, the probe pressure is converted to intraocular pressure in block 309 in FIG. 3A using a probe-specific lookup table or analytic expression. An example of an analytic expression that may be used to convert probe pressure to IOP is the previously noted expression: PP=1.96(IOP)+1.75, where PP is the probe pressure and IOP is the eye pressure. The IOP as a function of time 600 in the region of interest is shown in FIG. 6.

The program proceeds from FIG. 3A to FIG. 3B as indicated by block 310 in FIG. 3A and block 311 in FIG. 3B. A straight-line regression then is performed in block 312 in FIG. 3B. A first order polynomial initially is fitted to the data. Then the mean IOP is determined in block 313. The IOP value at the center of the straight-line fit to the ROI is the mean IOP.

The software then fits a 3rd order polynomial to the pulsatile ROI in block 314. See FIG. 6, which shows a 3rd order polynomial curve 602 fitted to the ROI after the raw data are converted from probe pressure 400 to IOP 600. The 3rd order curve 602 generally runs through the inflection points of the oscillatory portion of the IOP waveform 600 in FIG. 6. The 3rd order polynomial found above is subtracted from the truncated data in block 316 to remove the DC offset and any overall tendency of the data to slope or curve. This results in flattened and zero-based IOP data 700 in FIG. 7.

Next in FIG. 3B, the peaks 704 and valleys 706 shown in the IOP data are identified in block 318. First, a copy of the data is created, which is then smoothed. That data is then differentiated. After differentiation, any zero-crossings correspond to peaks and valleys in the original data. The peak detection circuit has tunable amount of noise-suppression. All instances of smoothing in the code use the same subroutine that implements boxcar smoothing described above, with the possible exception of differing boxcar lengths depending on how much tolerance there is for smoothing. The subroutine thus takes a smoothing length as a parameter.

The first step in the peak-finding process in block 318 is to smooth the IOP data 700 because the next step is to differentiate the data, which by its nature tends to amplify noise. The smoothing can be fairly aggressive at this point since the only interest here is in finding where in time the true peaks are, not what their amplitudes might be. Differentiation transforms a signal to something that represents the local slope. A local extremum (peak or valley) can only occur when the slope is zero. Having smoothed the input data and then differentiated it, the computer 122 searches for where the signal goes to zero. Since there are only a limited number of data points, it is unlikely that any single data point will actually equal zero, and there could be several points competing for the title of closest to zero. Also, the computer 122 determines whether a zero is a peak or a valley. To accomplish this, the computer 122 in block 318 constructs another boxcar, which it slides along the differentiated signal while monitoring whether its polarity is negative or positive. It does not matter what the average value is, just whether the average is positive or negative. At the moment that the average computed by the boxcar in block 318 changes polarity, the boxcar is centered on the zero point. If the result of the boxcar computation is going from positive to negative, then the boxcar is centered on a peak; if result of the boxcar computation is going from negative to positive, then boxcar is centered on a valley.

In block 320 in FIG. 3B, the positive peaks in the IOP data found in block 318 are averaged to produce a mean positive peak; the negative peaks in the IOP data are averaged to produce a mean negative peak. The computer 122 subtracts the mean negative peak from the mean positive peak to obtain the pulse amplitude.

Figure 7:
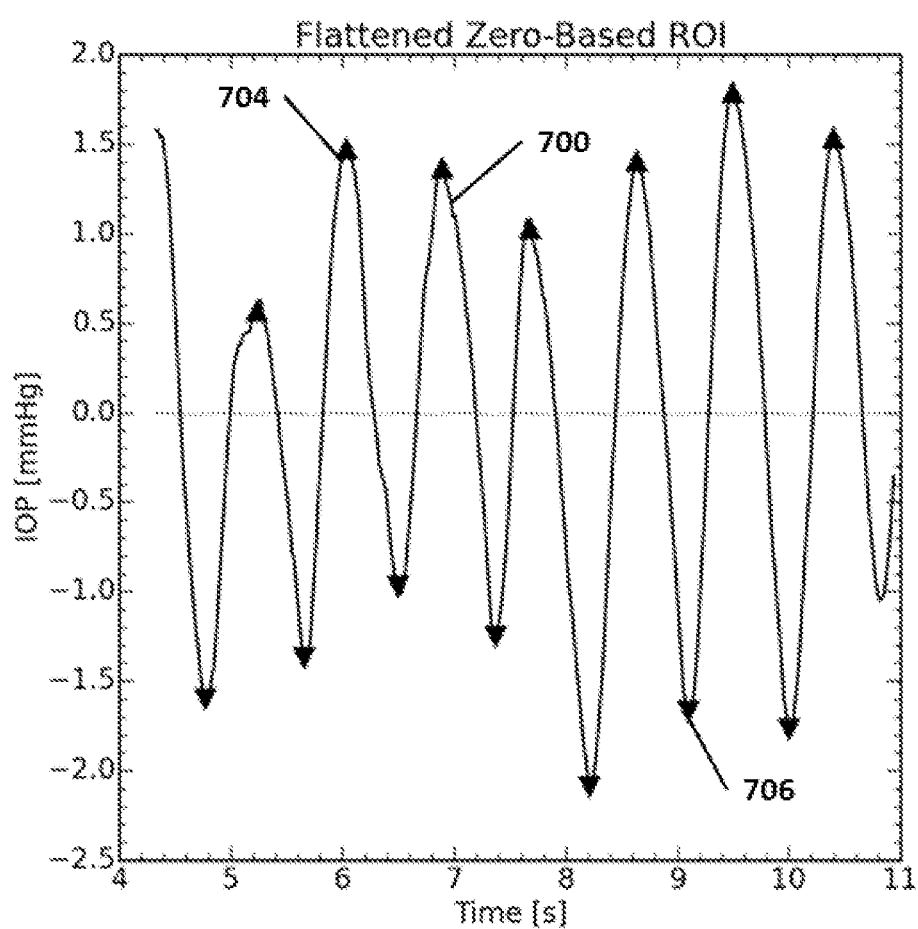
FIG. 7 is an illustrative plot of a flattened zero-based region of interest derived from the intraocular pressure plot of FIG. 6 with the results of a peak finding process indicated on the plot.
Figure 8:
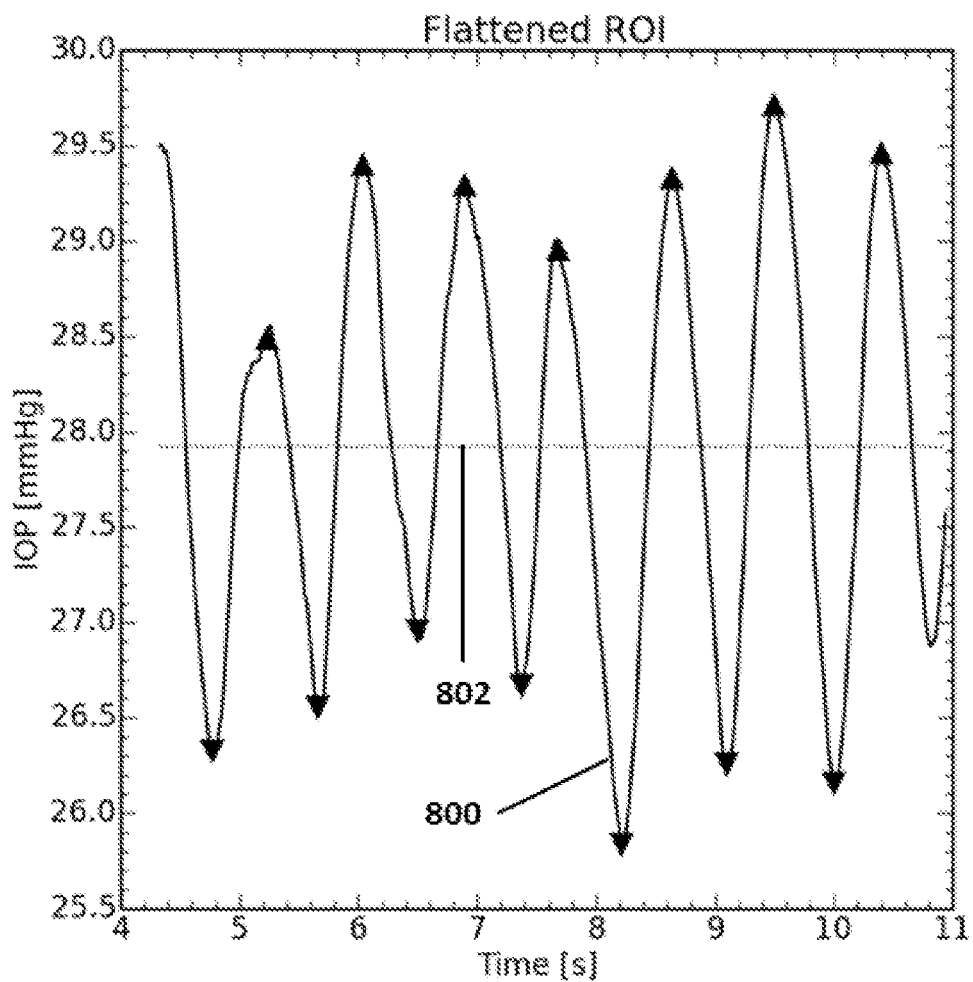
FIG. 8 is an illustrative plot of a flattened IOP pulsatile region in an intraocular pressure plot based on the zero-based region of interest in the intraocular pressure plot of FIG. 7 with the results of a peak finding process indicated on the plot.

The mean IOP computed in block 313 is added to the flattened zero-based IOP data of FIG. 7 in block 321 to obtain a flattened IOP pulsatile region 800 shown in FIG. 8. The horizontal line 802 in FIG. 8 represents the mean IOP added to the flattened zero-based IOP data in FIG. 7.

The program proceeds from FIG. 3B to FIG. 3C via blocks 323 and 324. The mean pulse rate is found in block 325 in FIG. 3C, for example, by counting the number of positive peaks in the ROI and dividing the number of positive peaks minus one by the time between the first and last peaks. Formally, the pulse rate PR is as follows:

$$PR=(n_p-1)/(t_n-t_0),$$

where $n_p$ is the number of peaks, $t_n$ is the time of the last peak, and $t_0$ is the time of the first peak.

Using the Silver and Geyer relationship between IOP and eye volume (Silver & Geyer 2000), the time-dependent change in volume ΔV of the eye in response to the pulsatile signal is found by the computer 122 in block 326 in FIG. 3C. Eye volume is based on averages given by Silver and Geyer for males and females, and sex selection in the software. According to Silver and Geyer, for the average human, the change in eye volume is:

$$\Delta V=-49.8+30.2 \ln P+0.242P, \qquad (1)$$

where ΔV is the change in volume and P is the IOP. For males, the equation is:

$$\Delta V=-52.2+31.7 \ln P+0.254P \qquad (2)$$

The corresponding equation for females is:

$$\Delta V=-47.4+28.7 \ln P+0.230P \qquad (3)$$

Figure 9:
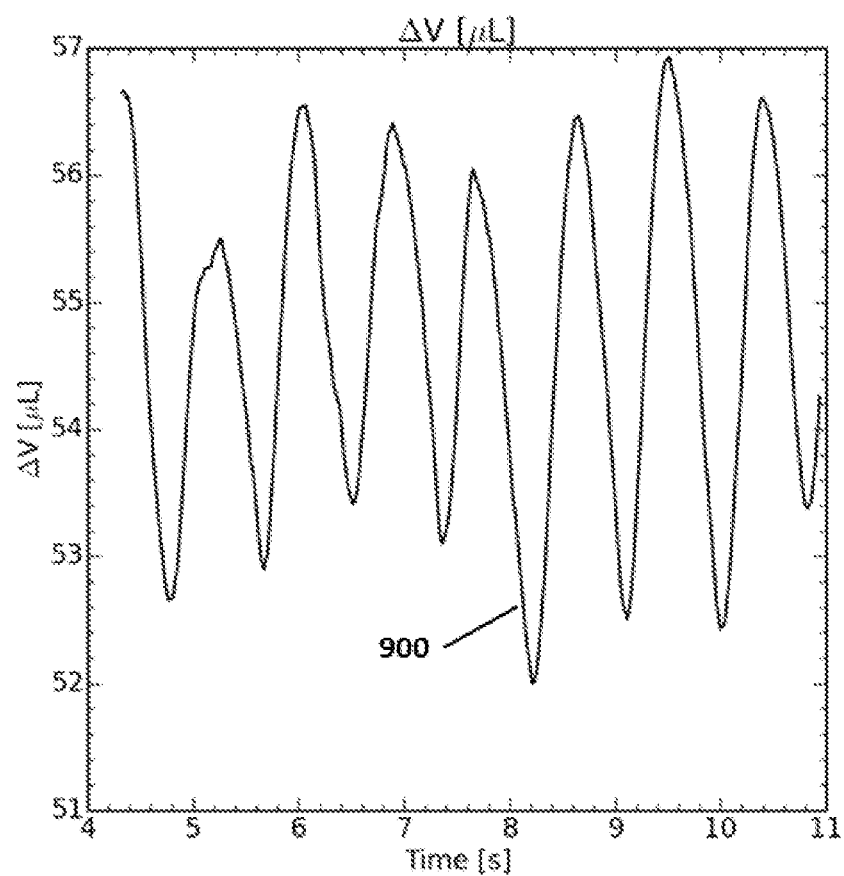
FIG. 9 is an illustrative plot of the change in ocular volume as a function of time based on the IOP data shown in FIG. 8.

FIG. 9 shows an IOP pulsatile signal that has been translated into change in eye volume curve 900 by applying the pressure-volume relationship (1) above. Relationships (2) and (3) could also be applied. Thus the oscillations in FIG. 9 are in terms of eye volume, not pressure.

Figure 10:
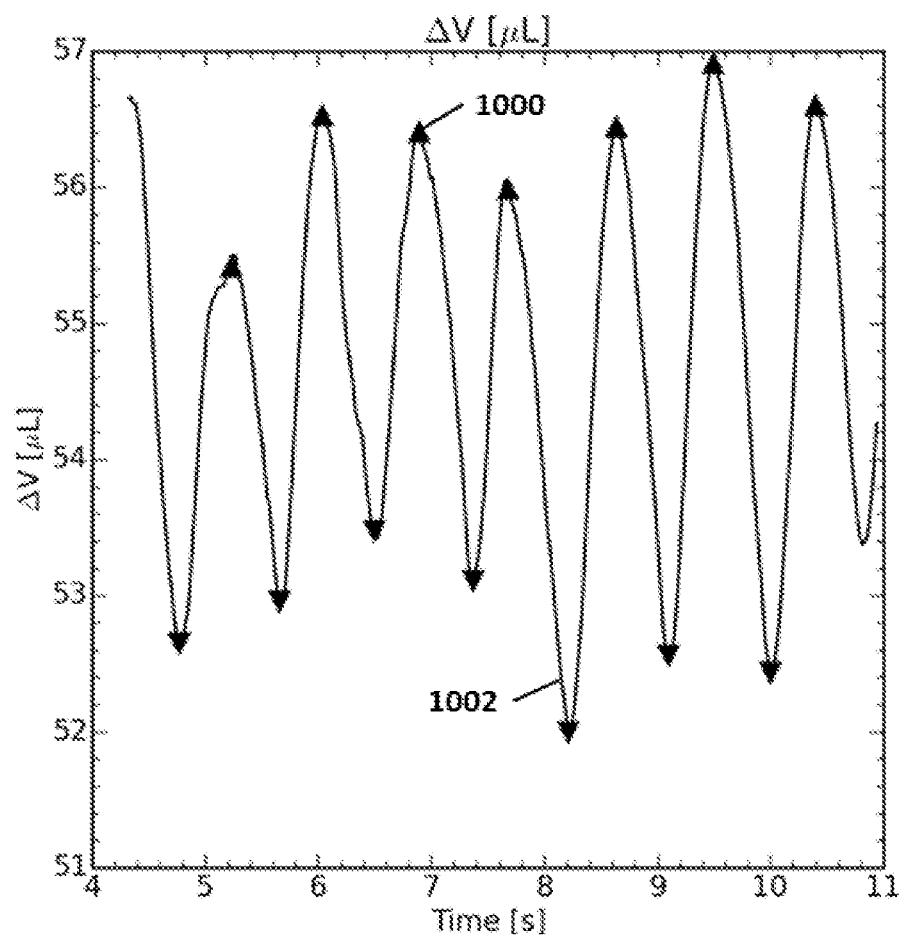
FIG. 10 is an illustrative plot of the change in ocular volume as a function of time shown in FIG. 9 with the results of a peak finding process indicated on the plot.
Figure 11:
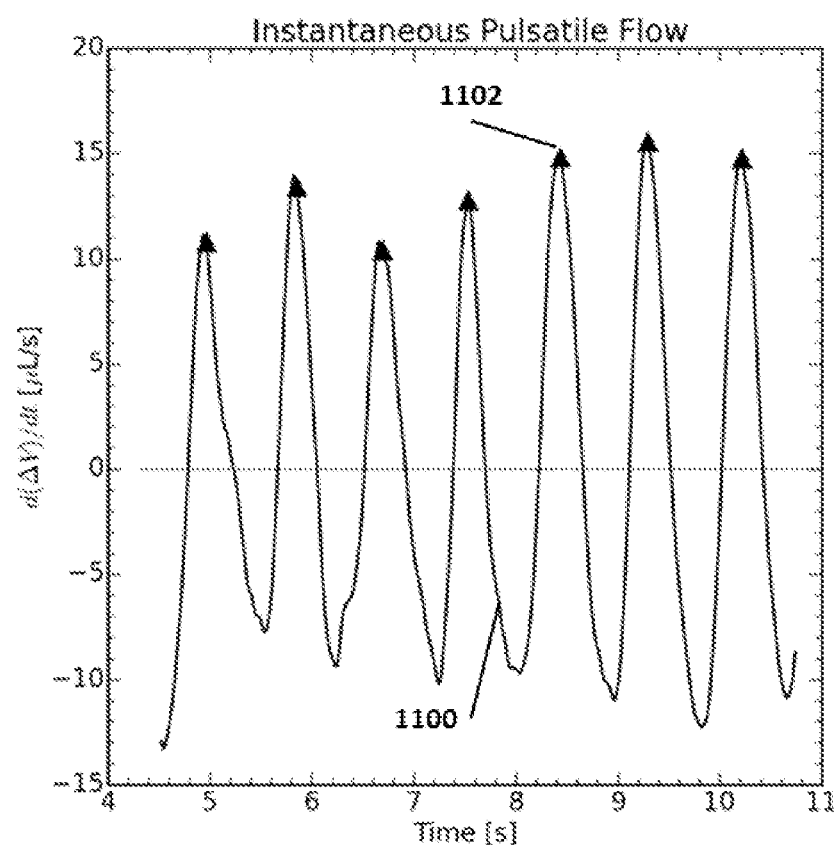
FIG. 11 is an illustrative plot of the derivative of the change in ocular volume as a function of time of FIG. 10 with the results of a peak finding process indicated on the plot.

In block 328, the positive peaks 1000 and the negative peaks 1002 in the ΔV data shown in FIG. 10 are found and averaged. The computer uses the peaks found in block 322 to perform the averaging in block 328. Peaks in the IOP data occur at the same time coordinates as the peaks in the delta-V data, since the transformation to delta-V data affects only the dependent variable, not the time variable. So, the computer looks at the value of the delta-V data at the time coordinates found in block 322. The negative mean peak is subtracted from the positive mean peak to obtain the mean peak-to-peak pulsatile ΔV. In block 330, the mean ΔV above is divided by the mean pulse duration to obtain the Net Pulsatile Flow. This is computed both in terms of μL/s and μL/min. The ΔV data is differentiated in block 332 to get the instantaneous rate of change of volume: d(ΔV)/dt, the results of which are shown as curve 1100 in FIG. 11. Smoothing similar to that described above is performed here as well for noise suppression. Again, there is a trade-off between getting reliable data and impact on the magnitude of the data. The positive peaks of d(ΔV)/dt 1102 are found and averaged in block 334. This average is the mean instantaneous Peak Net Pulsatile Flow. This also is computed both in terms of μL/s and μL/min.

The Mean IOP, Pulse Rate, Pulse Amplitude, Net Pulsatile Flow, and the Peak Net Pulsatile Flow are presented for display in block 336. This blood flow data may be presented on any display, for example, a computer display, in graphical or numerical form. An illustrative numerical display is shown in FIG. 12.

The software in computer 122 computes various ocular perfusion pressures in block 336. The computer 122 acquires the systolic and diastolic components of the patient's arterial blood pressure, SBP and DBP, respectively. These numbers may be determined through the use of a traditional sphygmomanometer or electronic blood pressure measurement apparatus and entered into the computer 122 by the operator of the blood flow measurement system. The computer 122 generates the mean ocular perfusion pressure in accordance with the following relationship:

$$\text{mean OPP}=2.0/3.0*(DBP+1.0/3.0*(SBP-DBP))-\text{mean IOP.}$$

The computer 122 also generates the systolic ocular perfusion pressure in accordance with the following relationship:

$$\text{systolic OPP}=SBP-\text{mean IOP,}$$

and the diastolic ocular perfusion pressure in accordance with the following relationship:

$$\text{diastolic OPP}=DBP-\text{mean IOP.}$$

These three ocular perfusion pressure measurements are sent for display in block 337.

Signal Processing Embodiment 2

Figure 13:
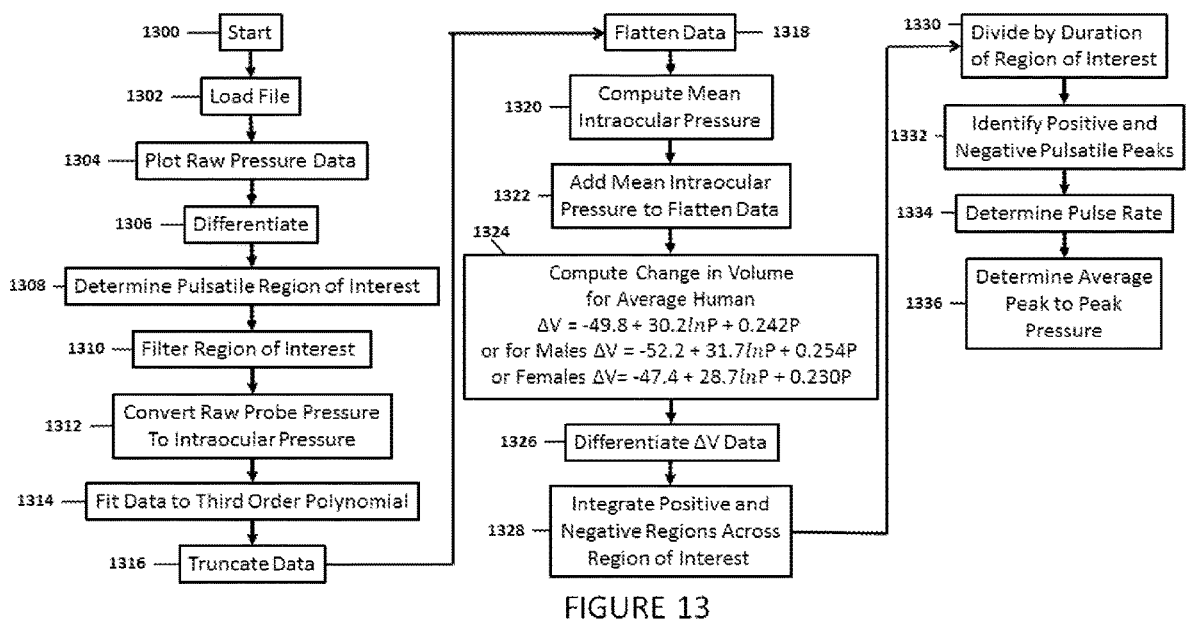
FIG. 13 is a flow chart depicting the operation of another example of the software in the computer shown in FIG. 1.
Figure 14:
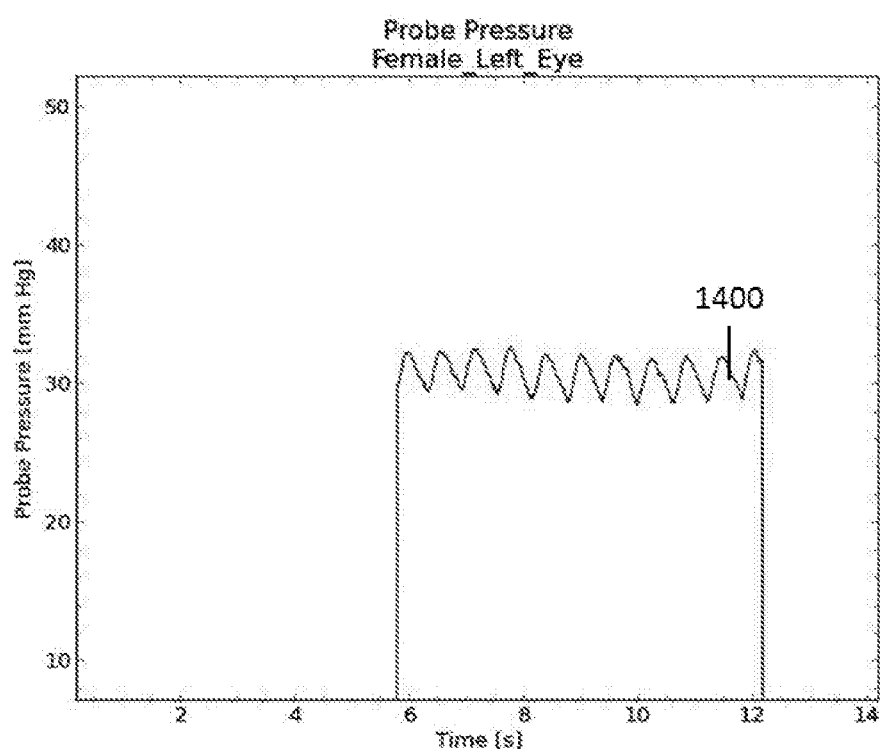
FIG. 14 is a plot of probe pressure obtained as a result of an illustrative second eye examination.

FIG. 13 is a flow chart depicting in detail the operation of the software in the computer 122 that performs the signal processing part of this invention in accordance with a second example of the software. The program begins in start block 1300. Next, in block 1302, the program loads into memory a text file of raw probe pressure data collected from the probe 112. After loading the text file of data, the software, in block 1304, creates a plot of the raw data as a function of time 1400, as shown in FIG. 14.

Figure 15:
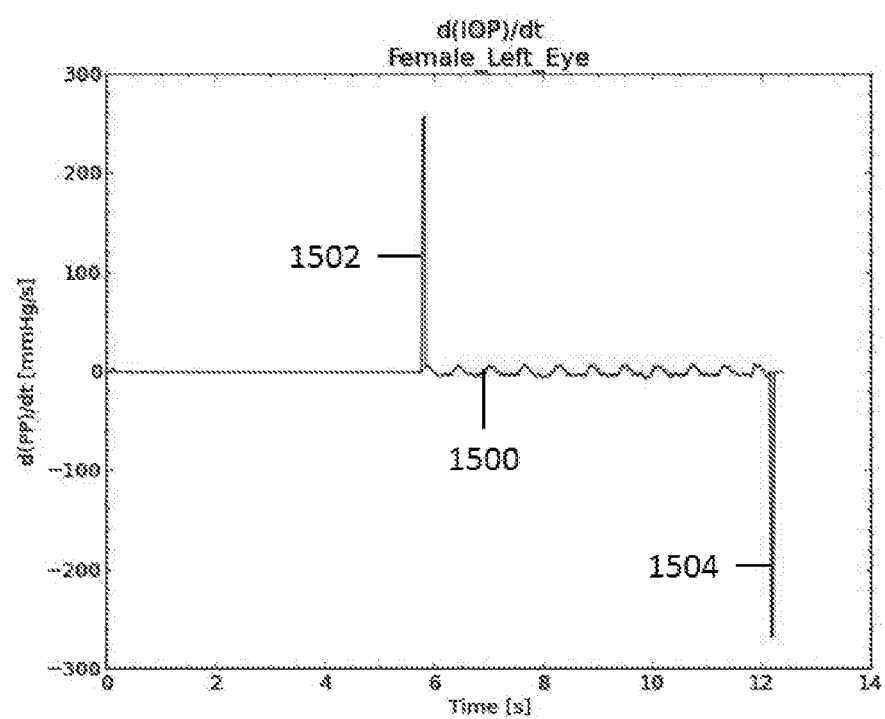
FIG. 15 is an illustrative plot of the derivative of the probe pressure data in FIG. 14.

Next, the software automatically senses the onset and the end of the pulsatile regions of interest (ROI). This is done by differentiation of a smoothed version of the input signal in block 1306. A differentiated signal is one that represents the local slope of the original signal. The slope of the pulsatile region never exceeds a certain value, but when the measurement begins, and when the measurement ends, there is a rather large slope change, positive at the beginning of the ROI, then negative at the end of the ROI, respectively. FIG. 15 shows the differentiated raw data 1500. Regions of high value 1502 and regions of low value 1504 correspond to regions of highly positive and highly negative slope, respectively, in the raw probe pressure data. Such regions only occur at the onset and termination of the measurement, in other words at the beginning and end of the region of interest.

These uniquely high slope regions may be sensed in block 1308 by a thresholding method, giving the onset and end of the pulsatile region of interest (ROI). The software compares the values of the differentiated raw data and compares them to positive and negative thresholds. When the positive threshold is exceeded, the software has identified the start of the measurement. When the differentiated raw data is less than the negative threshold, the end of the measurement has been identified. The pulsatile region of interest is between the beginning and end of the measurement.

Figure 16:
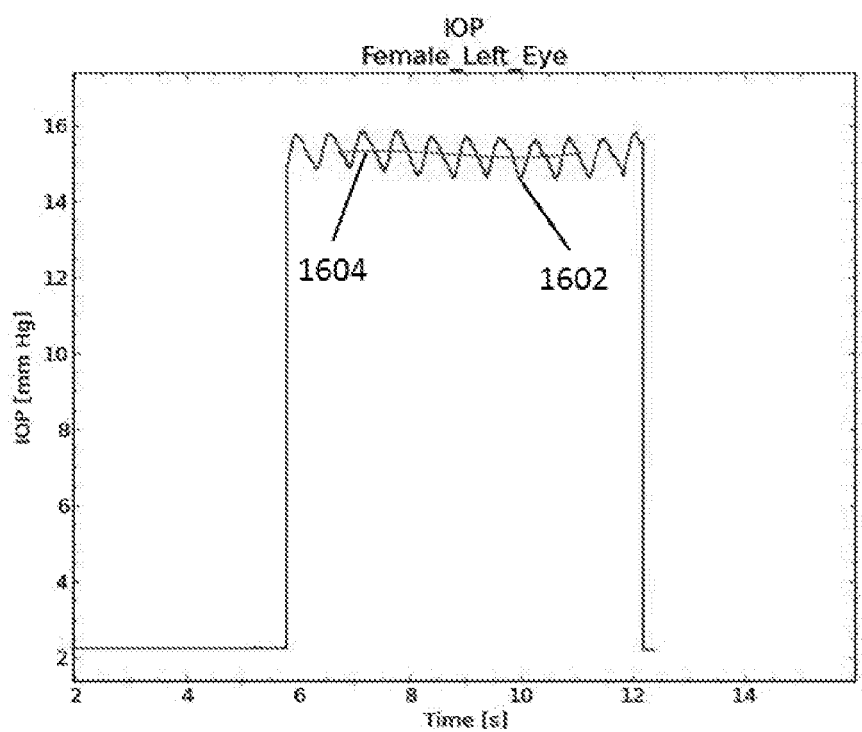
FIG. 16 is an illustrative plot of the intraocular pressure data of FIG. 14 to which a third order polynomial has been fit.

The software then restricts the raw pressure data by contracting the found ROI by about one second, in block 1310, to be sure that the region being sampled truly represents the pulsatile region, and does not contain any excessive signal due simply to onset or termination pressure fluctuations. Now the probe pressure is converted to intraocular pressure in block 1312 either using a probe-specific lookup table or analytic expression. FIG. 16 shows an illustrative intraocular pressure curve 1602 corresponding to the probe pressure curve 1400 in FIG. 14. The software then fits a 3rd order polynomial 1604 to the pulsatile ROI in block 1314. See FIG. 16, which shows a 3rd order polynomial curve 1604 fitted to the ROI after the raw data are converted from probe pressure to IOP. The 3rd order curve generally runs through the inflection points of the oscillatory portion 1602 of the waveform in FIG. 16.

Figure 17:
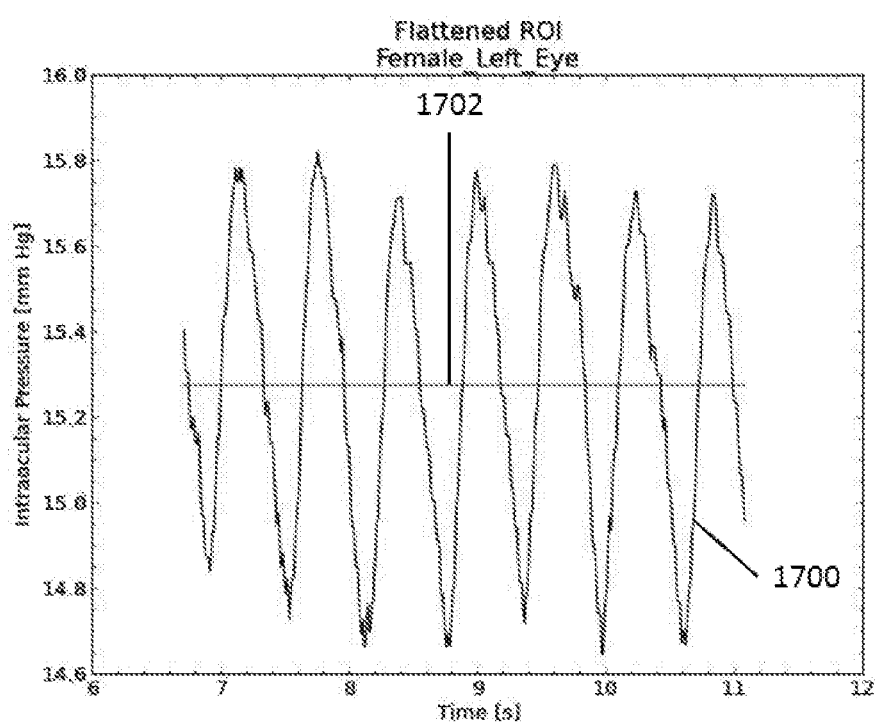
FIG. 17 is an illustrative plot of a flattened region of interest in an intraocular pressure plot of FIG. 16.

There is no further need for the entire data set, so the software now truncates the data in block 1316 to include only the ROI, and the 3rd order polynomial found above is subtracted from the truncated data in block 1318 to remove the DC offset and any overall tendency of the data to slope or curve thereby creating a zero-based flattened ROI. The mean IOP across the ROI is then computed in block 1320 and added back to the signal in block 1322 resulting in a flattened ROI at the mean IOP pressure. See FIG. 17, which shows a flattened ROI 1700. The mean IOP, represented by the horizontal line 1702, has been added back to the zero-based ROI derived in block 1318 to obtain the flattened ROI 1700 in FIG. 17.

Using the Silver and Geyer relationship between IOP and eye volume (Silver & Geyer 2000), the time-dependent change in volume of the eye in response to the pulsatile signal is found in block 1324. Eye volume is based on averages given by Silver and Geyer for males and females, and sex selection in the software. According to Silver and Geyer, for the average human, the change in eye volume is:

$$\Delta V=-49.8+30.2 \ln P+0.242P, \quad (1)$$

where ΔV is the change in volume and P is the IOP. For males, the equation is:

$$\Delta V=-52.2+31.7 \ln P+0.254P \quad (2)$$

The corresponding equation for females is:

$$\Delta V=-47.4+28.7 \ln P+0.230P \quad (3)$$

Figure 18:
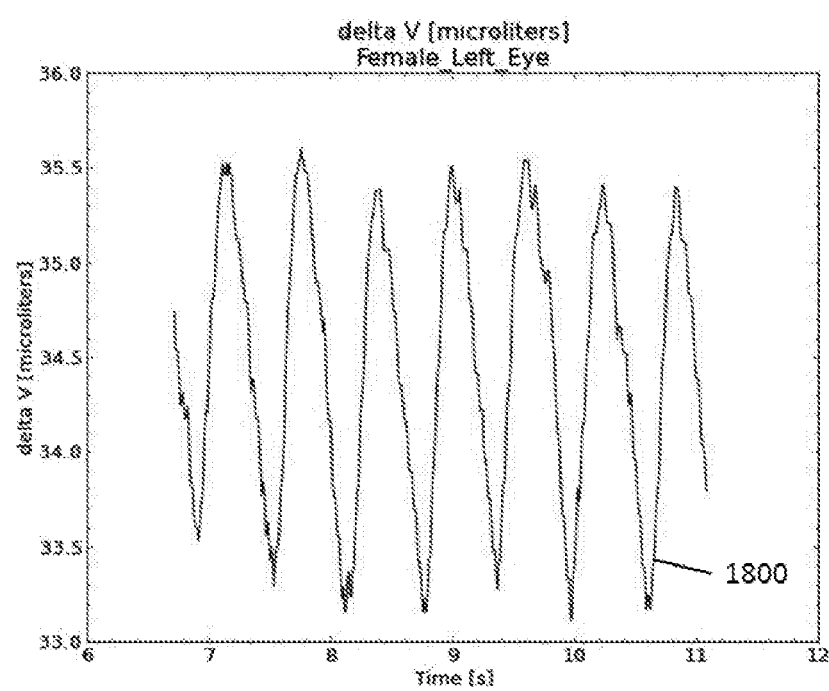
FIG. 18 is an illustrative plot of the change in ocular volume as a function of time based on the IOP data of FIG. 17.

FIG. 18 shows an IOP pulsatile signal translated into change in eye volume curve 1800 by applying the pressure-volume relationship (1) above. Relationships (2) and (3) could also be applied. The oscillations are now in terms of eye volume, not pressure.

Figure 19:
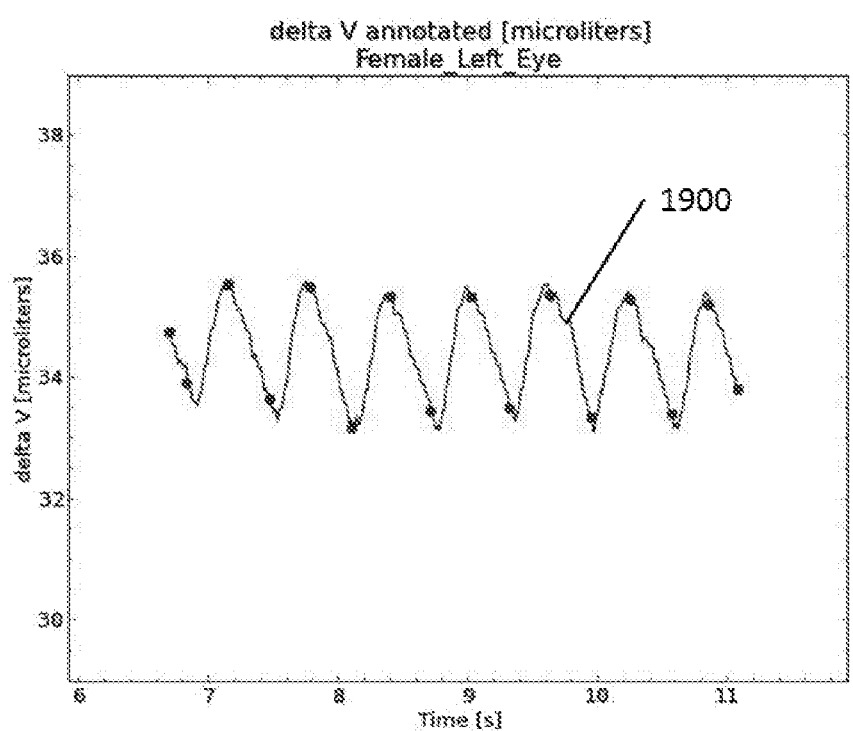
FIG. 19 is an illustrative plot of the change in ocular volume as a function of time shown in FIG. 18.

The varying volume signal found above is now smoothed and differentiated in block 1326 to get the instantaneous pulsatile flow as a function of time. Then, the positive regions are integrated in block 1328 across the ROI to obtain the net pulsatile inflow, which is then divided by the duration of the ROI in block 1330 to get a pulsatile inflow rate in μL/s. The same process is applied in block 1330 to the negative regions in block 1328 to obtain the net pulsatile outflow and the pulsatile outflow rate. See FIG. 19. Of course, the inflow and outflow are expected to sum to (nearly) zero. FIG. 19 shows the instantaneous pulsatile flow curve 1900. The positive regions are integrated and averaged to get the average inflow rate; the average outflow rate is found in a similar manner with respect to the negative regions.

Figure 20:
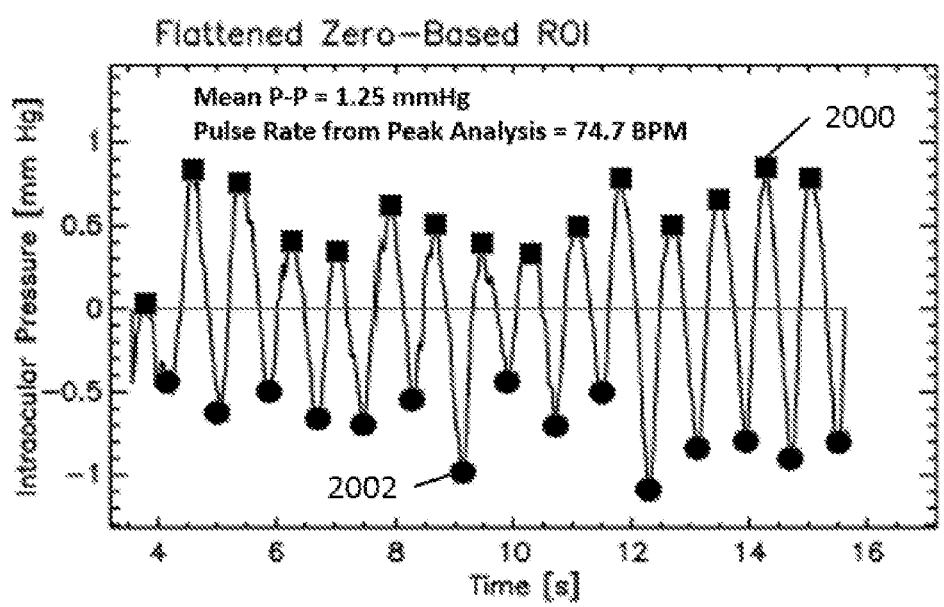
FIG. 20 is an illustrative flattened zero-based plot of intraocular pressure as a function of time showing the operation of a peak finding process.

Finally, the zero-based flattened IOP derived in block 1330 is smoothed and differentiated in block 1332 to identify the positive and negative pulsatile peaks. Knowing these pulsatile peaks allows one to determine and the average peak-to-peak pressure and the pulse rate. FIG. 20 shows both the positive peaks 2000 and the negative peaks 2002 in the flattened, zero-based IOP region of interest identified by the peak-finding process. This yields both the pulse rate in block 1334 and the mean peak-to-peak pressure in block 1336. The blood flow data and the curves derived by the digital signal processing circuitry of FIG. 13 may be displayed on a computer display or may be numerically displayed as illustrated by FIG. 12.

Although not shown in the flow charts of FIGS. 3A-3C and 13, Gosling's pulsatility index data may be derived from the described data generated by the software in the computer 122. Gosling Pulsatility Index (PI) is a measure of the variability of blood velocity in a vessel, equal to the difference between the peak systolic and minimum diastolic velocities divided by the mean velocity during the cardiac cycle. The equivalent Gosling pulsatility index is based on flow rather than velocity.

Illustrative Equipment

Illustrative electronic equipment that may be used to implement the ocular blood flow measurement system shown in FIGS. 1, 2, 3A-3C, and 13 include a computer 122 in the form of a Raspberry Pi microcomputer running a fully functional desktop operating system. Alternatively, in prototyping environments, the computer 122 may be implemented as a series connected Raspberry Pi and an Arduino micro controller, the Arduino being in series with the Raspberry Pi between the pressure sensor 112 and the Raspberry Pi to provide shielding for the Raspberry Pi. The electronics that processes the data generated by the apparatus of FIGS. 1, 2, 3A, 3B, 3C, and 12 does not have to be a computer. The suitable electronics may be any form of signal processing circuitry that is capable of producing the results described herein.

The brushless DC motor 102 and pump 104 may be a Series 1410VD, Model 14100216, diaphragm pump with integral brushless DC motor, made by Gardner Denver Thomas, Inc. of Sheboygan, Wisconsin. The pressure compensated flow controller 108 may be a Model PCFCD-1N1-E BRS, pressure compensated flow controller, made by Beswick Engineering Co., Inc. of Greenland, New Hampshire. The pressure sensor 116 may be a Model MS4525 printed circuit board mounted pressure transducer, made by Measurement Specialties of Fremont, California.

Operational Discussion

The basis of the device operation is to contain and measure pressure within a column of gas, for example, air, that varies in flow and pressure only as a function of the source pressure and resistance encountered at the distal end of a hollow tube 212 and nozzle 213 vented to the atmosphere by holes 236 in the tip 228.

The gas enters the probe body 200 through an inlet tube 208. Initially it flows through the probe body 200 via a hollow passage or pressure chamber 202, and into and through a shaft 212, into and through the unobstructed probe tip via a jet or nozzle 213 at the distal end of the shaft 212. The pressure in the probe body is low at this point as no major obstruction is present other than the size restriction of central passage 222 and the nozzle 213.

Before eye contact is made, probe 112 is in a free flow condition, or as close to a free flow condition as is allowed by particular proportions of the probe used. A forward motion of the shaft 212 occurs at approximately 10-20 mmHg in this condition. This is because the difference in surface area of the proximal end of shaft 212 central passage 222 creates an opposing surface which allows a portion of pressure in the probe body 200 to exert itself against the rear of the shaft 212. Greater pressure and flow in free flow condition results in proportionally greater forward thrust of the shaft 212. Greater pressure and lower flow caused by opposing exit of air from tip 228 by contact with the eye causes a similar increase in thrust against the eye by probe tip 228. Equilibrium is achieved when air pressure causes deflection of the cornea allowing a gap between the membrane 232 and nozzle 213 in probe tip 228. A softer eye allows a gap to form sooner at a lower pressure and flow. A harder eye resists the formation of a gap more strongly, resulting in a gap forming at a higher pressure and flow, as well as a greater forward pressure of the entire probe/tip assembly 112/228.

The pressure in probe body 200 increases in a known manner, for example, proportionally, in response to the resistance to flow caused by an individual eye against the tip 228 and nozzle 213. A standing column of air pressurizes tube 210 (interchangeable with tube 208 as aerodynamics and laminar flow are not considered or incorporated in the design), at the same pressure as the probe body cavity 202. This standing column of air communicates via a flexible tube to a micro machined silicon based pressure sensor 118 capable of hundredths of a mmHg pressure change sensing. Instead of a flexible tube connecting the pressure sensor to the probe, the pressure sensor 118 may be directly mounted on the probe.

Accuracy and time elapsed while acquiring a steady measurement are affected by user technique, unique characteristics of the eye, change in the eye caused by the measuring process, and constant changes in alignment of the probe nozzle 213 with the surface of the cornea causing variable pressures, and with changing IOP caused by the measuring pressure eliciting physiological changes in the IOP. The axis of nozzle 213 should intersect the cornea chord at 90 degrees to ensure a gap develops that is uniform around the entire perimeter of jet 213. A misalignment causes a leak-down of pressure readings, accompanied by initial difficulty in obtaining a repeatable, sustainable and measurable pressure rise and fluctuation over time. Effect of increased forward pressure of the shaft tip combination on the eye at higher pressures is to increase the ease of measuring, but it increases the applanation of the cornea and results in distortion of the eye and may cause egress of fluid through the outflow channels of the eye.

The user must rely more on tactile feedback than any self-regulation of the amount of probe extension. Greater ease of measurement is desirable as it results in shorter contact time with the eye, less opportunity for the eye to adapt to the measuring forces, and increased safety margin. Greater ease of measurement is obtained at greater flow and pressure, but may be undesirable in terms of accuracy of measurement and distortion of the eye.

Pressure changes are transmitted through tube 210 to the silicon based micro-machined pressure sensor. In illustrative examples, an on board ASIC (digital signal processor) within the sensor 118 encodes the pressure readings at a rate of 100 per second. This is approximately twice the resolution and accuracy needed to faithfully report the pressure variations in chamber 202. A digital data stream is transmitted to a computer software module where the data is captured to a file. On obtaining a clean measurement, the probe is removed from the eye, pressure drops as probe resumes free flow mode, and recording ceases. A second software module is launched and auto loaded with the most recent data capture file. An analysis of the data is made by novel software. The results, including pulse amplitude, pulse rate, pulse blood flow/second, pulse blood flow/pulse, OPP, SPP, and DPP may be printed to screen, showing a user report along with a graphic depiction of the wave form analyzed.

Comparative Evaluation

Apparatus in accordance with this invention immediately acquires measured pressure conditions, and produces a stable average pressure over time, as compared to the results obtained by the prior art devices.

The description above deals with a device to measure and analyze composite pulsatile blood flow to the eye including both choroidal and retinal components. All analysis herein is based on measurements of the variation in intraocular pressure known as IOP caused by "heart beats". Challenges to accurate measurement of IOP exist. Thus far the only method capable of measuring choroidal blood flow is the pneumatic tonometer. Two examples of this type of machine exist in the prior art, but they were unsatisfactory and neither is in production at this time. A renewed interest by researchers led to obtaining and testing several of the prior machines. They were built 10 or more years ago and contain components that are obsolete, and software used by the machines to collect and analyze data is specific to the obsolete components. Each instrument intermittently or consistently produces clinically significant variation in measurement. In addition, the instruments are difficult to use because they react to very small disturbances that are usually present during an eye exam. It was decided to create a new machine based on the basic principles of a pneumatic tonometer using current technology to compare data collected by the new machine to the data collected by the previous machines in an attempt to identify, understand, and correct the observed errors and data variability.

There were two main types of OBF machines in the prior art. One was developed by Dr. Maurice Langham and then marketed by Dr. Langham and his successors in interest. The other type of machine was marketed by Paradigm. See, for example, U.S. Pat. Nos. 4,883,056 and 5,857,969.

All the machines have a tip and membrane assembly that constrains the airflow by initial resistance of the tip itself when the tip is not in contact with the eye. When the probe contacts the eye, the eye/membrane interface is deformed so as to remove the constraint against the escape of air from the probe. Pressure in the probe is intended to have a linear relationship to IOP at a higher pressure than the eye itself. An initial pressure and flow is set at the air source to provide a constant component of thrust of the probe/plunger toward the eye. Without this pressure the probe will not engage with the eye surface; no measurement would occur. The base pressure set with no eye contact is a critical element, as are the pressure and flow across a full scale of 10 through 40 mmHg eye pressure.

Figure 21:
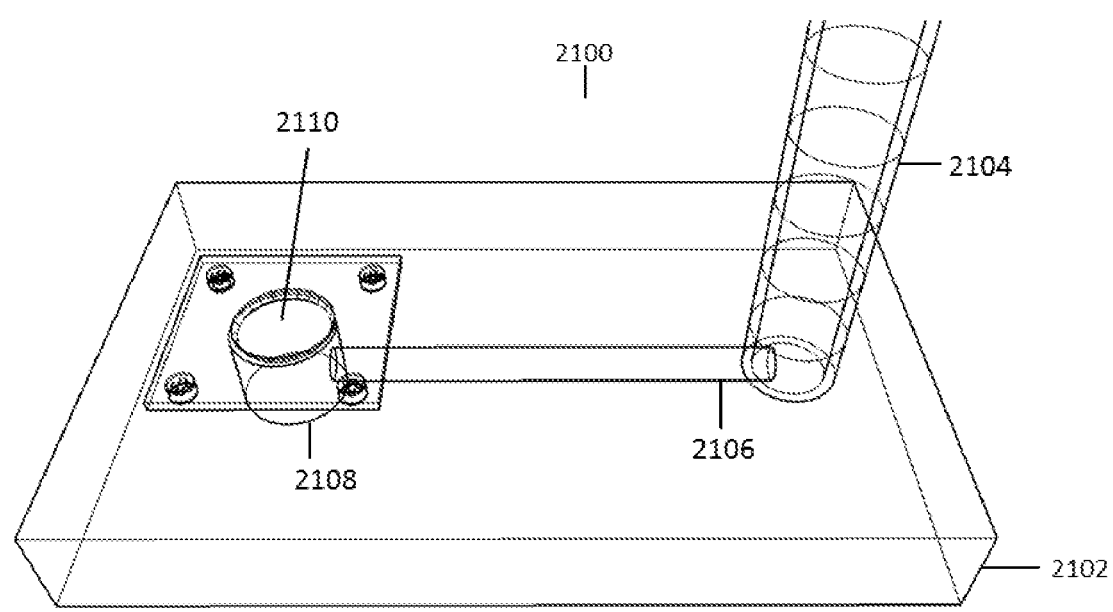
FIG. 21 is a perspective view of a manometer that simulates the pressure behavior of a human eye.

The measurements were taken by placing the probe tip onto a specialized manometer that has been calibrated and proven accurate as a proxy for a range of actual eyes. An example of such a manometer is shown in FIG. 21. The manometer 2100 comprises a base 2102 and a graduated cylinder 2104 set in the base 2102. The graduated cylinder 2104 contains a predetermined amount of fluid such as water. The bottom of the graduated cylinder communicates with one end of a horizontal passage 2106 formed in the base 2102. The other end of the passage 2106 is connected at its other end to a cylindrical pressure chamber 2108 formed in the base 2102. A flexible bladder 2110 analogous to the outer surface of a human eye seals the top of the pressure chamber 2108. The height of the fluid in the graduated cylinder 2104 is set such that the fluid pressure in the pressure chamber 2108 bearing against the bladder 2110 simulates the intraocular pressure in the human eye. The known fluid pressure against the bladder 2110 can be compared to readings obtained by the pressure measurement system described here when the pressure probe tip 114 is placed against the outer surface of the bladder 2110.

The prior instruments are difficult to use due to high sensitivity to user manipulation, faulty alignment, and motion of the eye during testing. These trace back to a very low starting flow achieved by restricting flow below the point where reliable measurement can be obtained consistently in the most critical range. In short, the backpressure on the probe is so small it allows disruption of eye/probe contact in response to very small operator inputs. Thus two measurements of the same eye pressure in the 10-17 mmHg range frequently result in order of magnitude differences in measured pressure. This includes the majority of patient IOP values. For example the Paradigm OBF machine reads a pressure of 7 mmHg consistently in a patient with a known IOP of 15 mmHg. Another patient measured at the same time with the same instrument measured correctly at 21 mmHg. Further exhaustive testing shows that measurement at or below 15 mmHg is subject to similar errors in other instruments of its type. This range of pressure is critical, as many patients would be misread using this instrument (Armaly, 1965).

Figure 22:
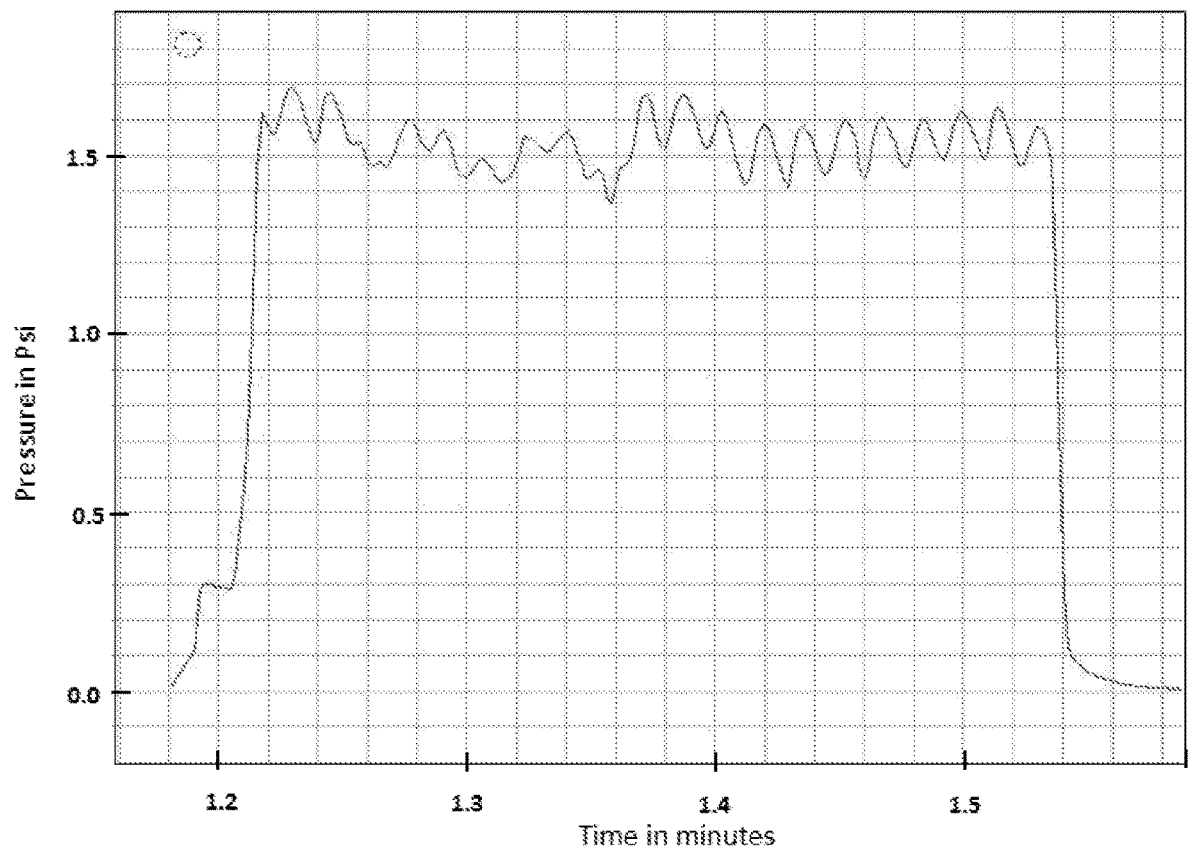
FIG. 22 is a plot of pulsatile eye data obtained from a prior art legacy machine.

Time to take a measurement and degradation of measured value over time also are problems with the prior instruments. The legacy units tend to experience a delay engaging with the eye at all, then produce and analyze a set of waves that are affected by perturbations of the user's hand. The waves also consistently follow a downward slope over time resulting from leakage around the probe. This is also an effect of limited volume of air to compensate for such phenomenon. See FIG. 22 showing an example of actual pulsatile eye data from a prior art machine. It clearly required a large amount of time to acquire clean uniform ocular blood flow pulses to analyze and then, even though the pulses were clean, the pulse amplitudes drifted over time. FIG. 22 is a typical good read from the prior art probe design, showing that the first 50% of probe contact with eye time is errata at probe contact, with a downward trend visible possibly due to probe pressure leakage or egress of fluid through the outflow channels of the eye.

Repeated error in measurement of the same patient, same eye, at the same time of day (actual eye pressure of 15 mmHg read as 7 mmHg) occurred. This error begins to occur at 15 mmHg and below. This comprises the majority of patients' IOP (Armaly, 1965). On close observation, while using a controlled air source, it appears that design of the tip is effective. Error and/or difficulty in measuring are attributed after experimentation to pulsation from the pump used to provide airflow and pressure. The pump in the prior art designs creates a noise threshold greater than the pulses in eye pressure to be measured. Running the pump so as to reduce the pulsations results in too little airflow to promote accurate measuring conditions. An attempt to solve the problem of pulsation from the pump involved filtering the pulsations by inserting a standard diaphragm type air pressure regulator with a 0-5 psi directly downstream from the pump. By nature, this type of device reduces the input pressure to a selectable maximum value at the output, regardless of changes in input pressure. If pressure on the output (eye facing) side of the system is reduced sufficiently to squelch noise, the flow that provides a robust contact with the eye is marginal at approx. 10 mmHg. On the other hand, increasing the output pressure results in too high probe pressure, and increases forward thrust of the probe tip into the IOP range. Obviously this would result in unintended applanation and defeat the operation of the probe tip, which is designed to operate with slightly above (approx. 10 mmHg) neutral pressure against the eye surface. This value is below most possible low IOPs, but flow is so low that accurate measurements are difficult to achieve, and the instrument is hypersensitive to misalignment or shake. This not a serious limitation because, clinically, the only time we need to measure pressure below 10 mmHg is when there is a surgical or trauma induced leak in the globe. Accuracy of measurement is rarely needed at less than 10 because we simply know we have to get the pressure higher or there will be bleeding inside the eye.

Figure 23:
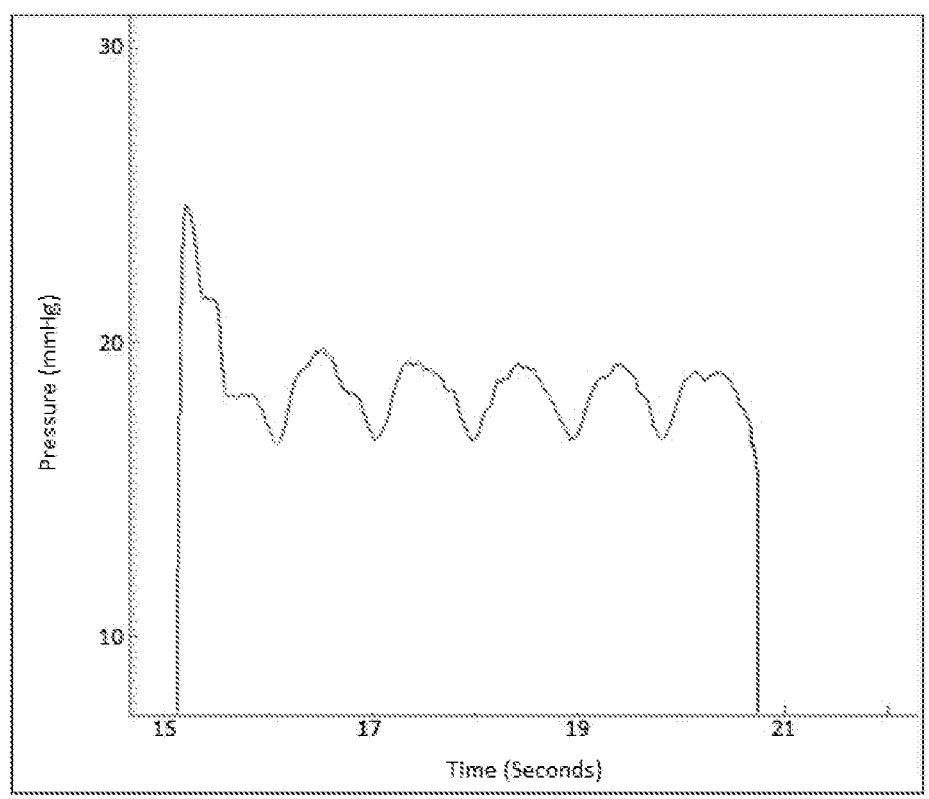
FIG. 23 is a plot of pulsatile eye data obtained from a machine in accordance with this invention.

Excessive pressure in the probe deteriorates accuracy and reliability when measuring lower eye pressures. The starting pressure of the probe, the component of forward pressure applied to the tip (and thus the eye) is too close to the actual eye pressure, resulting in a sharp deviation from a linear relationship needed for full scale measurements of a range of eye pressures at a critical range. This phenomenon is a result of compromise between accuracy and range of measurement possible using ordinary pressure regulation and static needle valve flow control as described above. Compare FIG. 22 showing the results for a prior art machine with FIG. 23 showing the results for a machine in accordance with the invention. Note the significantly less time to acquire clean pulses with the machine in accordance with the invention. The prior art tried to compensate for this with software but it was not successful because other parameters causing inaccuracy like user or eye movement could not be predicted on individual patients.

Figure 24:
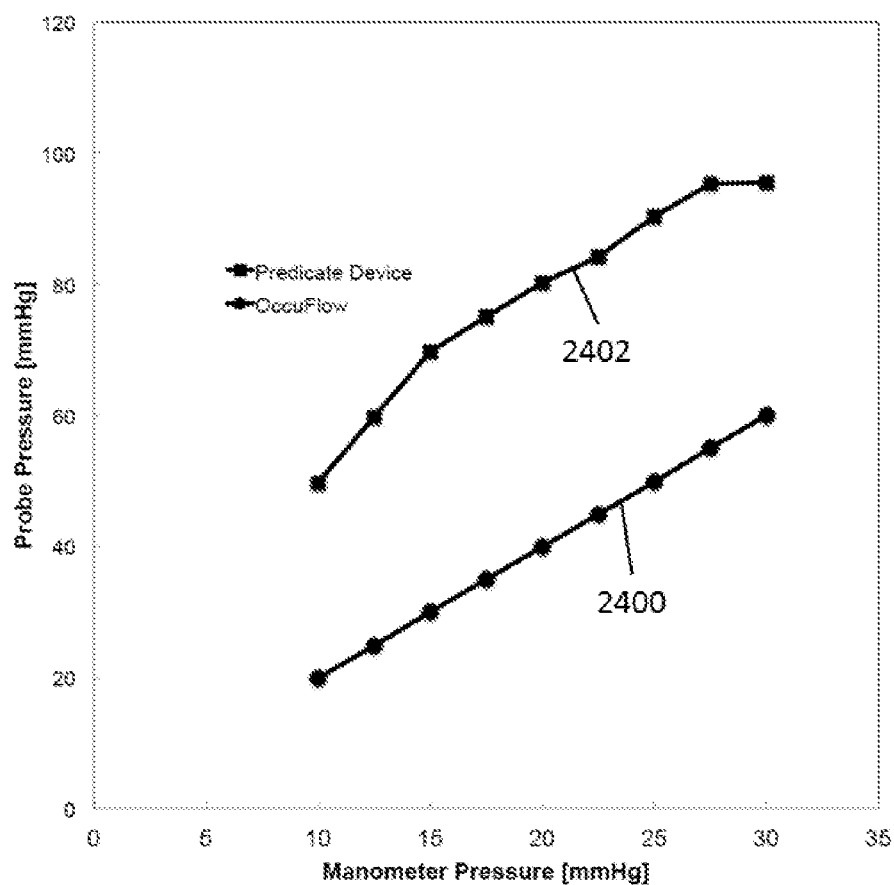
FIG. 24 is a graph illustrating and comparing the non-linearity of a prior art machine and the linearity of a machine in accordance with this invention.

Apparatus in accordance with the invention also is substantially more linear than prior art apparatus. Pressing the probe against a diaphragm type manometer that produces a known pressure that simulates actual IOP and plotting the pressure in the probe against the known manometer pressure illustrates the linearity of pressure measurements taken by a probe in accordance with the invention. The non-linearity of the prior art probe may be determined by doing the same thing with the prior art probe. FIG. 24 is a plot of probe pressure versus manometer pressure for both the probe in accordance with the invention and a prior art probe referred to as a predicate device. Curve 2400 represents the probe pressure versus manometer pressure for a prior art probe. Curve 2402 represents the probe pressure versus manometer pressure for a probe in accordance with the invention. The curves 2400 and 2402 illustrate that a probe in accordance with the invention is substantially more linear than the prior art probe in a range of 10-30 mmHg manometer pressure, which is where actual patient IOP's are expected. Note the sharp deviation from linearity in the 15 to 10 mmHg descending range of the prior art probe. Also, the pressure in the prior art probe is substantially higher than in the probe in accordance with the invention. For example, note the rather high probe pressure of 50 mmHg corresponding to 10 mmHg manometer pressure being measured. High probe pressures would cause more applanation of the eye and would possibly cause minor epithelial defects in the cornea that could possibly increase the risk of infection.

A new prototype machine was created with the objectives of testing the existing tips and probes with visibility into the nature of the wave forms representing ocular pressure, efficient data collection, and plotting in real time. Very accurate control over pressure and flow (volume) in the air supply was achieved by replacing the pressure regulator mentioned above with a pressure compensated flow control device 108 and using a more constant torque pump motor 102, specifically the newer generation DC motor called a Brushless DC Motor. The conjecture was that consistent flow control of air to the tip might result in substantially more repeatable accurate measurements without much effort or training on the part of the user, while providing full scale linear 10 to 40 mmHg measurements. This is counterintuitive, as a pressure compensated flow controller operates by increasing/decreasing pressure at the output to maintain a constant flow. The flow rate is pre-set using an integral user accessible needle valve and lock nut. A device that attempts to maintain constant flow in a system that measures pressure does not initially make sense. It would seem this technique would increase pressure independently of the measurement input from the probe tip. The hypothesis was that it would sustain repeatable constant flow across a full range of IOP/probe pressure while enabling a low pressure high flow initial calibration setting of the probe/air supply system. This theoretically would enable more consistent and repeatable measurements in the critical range of IOP from 15-17 mmHg. Results of experiments comparing the test prototype and the legacy machines proved that the test prototype device operates in a more consistent and reliable manner extending to lower IOP's, while also operating at an accurately controlled relatively low probe pressure. Manipulation of the probe shows a robust and repeatable contact with the eye that results in an immediate commencement of measureable pulse forms, without any special effort by the user.

The pressure compensated device 108 dampens noise more effectively than a pressure regulator because it can be preset accurately at a low pressure, but is designed to operate over a range of output pressures while maintaining constant flow, versus the pressure regulator, which seeks to maintain a constant pressure against any outside force from the eye. Use of a pressure compensated flow controller 108 maintains a linear relationship between eye and probe pressure reliably into the most important 10-17 mmHg ranges of IOP, as well as consistent measurements over the entire range from 10-40 mmHg.

Initially, the above experiments were performed with a standard DC motor/pump as used in the legacy instruments. A constant input pressure is difficult to obtain with this type of motor as it does not provide constant torque and therefore tends to produce variation in pressure under variable loads. Changing the pump motor to a brushless DC motor maintains consistent torque, providing a consistent input to the pressure compensated flow controller and a consistent outflow with the ability to set the outflow very accurately to obtain repeatable and accurate forward pressure on the probe/tip. This means a consistent measuring condition is maintained across a range of IOPs. Significant improvement in usability and repeatability resulted. See FIG. 23 for actual data plotted from the ocular blood flow device described herein.

FIG. 24 shows precise correlation in slope ratio between manometer and probe pressure with probe pressure needed to read 10 mmHg is 30 mmHg below the legacy probe pressure of 50 mmHg. Lower pressures may equate to a better margin of safety when exerting pressure on the eye with a stream of air. The probe pressure is a much more linear function of the intraocular pressure in the region where most patients measure, that is, in the IOP range of about 10 to 30 mmHg. Compare curve 2400 with curve 2402 in FIG. 24.

The quality of pulsatile eye pressure signals obtained by the device described herein is markedly different from that of the legacy units. Generally, devices in accordance with this invention attain contact with the eye and begin to measure immediately, with a constant steady signal waveform plotted. See FIG. 22. This waveform is of high resolution and maintains a steady value. Unlike the legacy device, the pulsations do not rise or fall once a measurement is attained. The present invention enables measurement of variations of intraocular pressure with high accuracy and repeatability to be obtained without undesirably large forces being exerted upon the eye.

Diagnostics

This patent document discloses a novel system that produces accurate, stable, and repeatable low distortion measurements of intraocular pressure as a function of time from which reliable data about ocular blood flow can be derived. Abnormal intraocular pressure and ocular blood flow can be an indication of abnormalities and diseases in not only the eye, but also in other parts of the body. A health care provider can assess the intraocular pressure and ocular blood flow data in conjunction with appropriate clinical correlation to identify those abnormalities and diseases. Clinical correlation may include other tests, observations, and historical patient information. For example, in the eye, a health care provider can detect glaucoma, macular degeneration, diabetic retinopathy, ischemic optic neuropathy, retinal venous occlusive disease, retinal arterial occlusive disease, retinopathy of prematurity, retinitis pigmentosa, and other ocular conditions. A health care provider can also use ocular pressure and blood flow data to help detect Alzheimer's disease, carotid occlusive disease, systemic disease, and cerebral vascular disease. Additional conditions that can be monitored by analyzing ocular pressure and blood flow data are burned skin, and the cerebral vascular flow, edema, and pressure associated with traumatic brain injury. Intracranial pressure in newborns can also be monitored in this way. Also, a health care provider can detect changes in ocular blood flow and can provide appropriate therapeutic interventions such as pharmaceuticals and surgery in response to changes in ocular blood flow.

APPENDICES

Appendix 1 below is a source code listing of a first example of a computer program written in the Python computer language that may be loaded onto the Raspberry Pi implementation of the computer 122 to accomplish the digital signal processing functionality described in FIGS. 3A, 3B, and 3C. Appendix 2 is a source code listing of a second example of a computer program that accomplishes the described digital signal processing functionality of FIG. 13.

CONCLUSION

The Title, Technical Field, Background, Summary, Brief Description of the Drawings, Detailed Description, and Abstract are meant to illustrate the preferred embodiments of the invention and are not in any way intended to limit the scope of the invention. The scope of the invention is solely defined and limited in the claims set forth below. It is intended, however, that the claims not be limited to any particular form of mechanical and electronic implementations. For example, implementations of the electronic portions of the invention may include any one or combination of hardware, software, and/or firmware. Also, although digital circuitry is preferred, analog circuitry may be used in all or any part of specific implementations within the scope of the claims.

The invention claimed is:

1. A composite ocular blood flow analyzer, comprising:
  a pressure probe adapted to be placed in contact with a human eye; and
  a pneumatic fluid supply adapted to supply pneumatic fluid to the pressure probe at a controlled constant fluid flow rate, in which the pneumatic fluid supply comprises:
  a pump having an output adapted to provide a pressurized flow of pneumatic fluid to the pressure probe for applying force to the surface of the eye; and
  a pressure compensated fluid flow rate regulator having an input and an output, the input of the pressure compensated fluid flow rate regulator connected to the output of the pump and the output of the pressure compensated fluid flow rate regulator connected to the probe, the pressure compensated fluid flow rate regulator adapted to provide a controlled constant fluid flow rate from its output to the probe regardless of pressure fluctuations.

2. The apparatus of claim 1, in which the pressure compensated fluid flow rate regulator comprises:
  a flow restrictor adapted to create a pressure drop that results in a desired fluid flow rate to the probe; and
  a compensation structure responsive to changes in the pressure drop created by the flow restrictor so as to maintain a constant fluid flow rate from the pump to the probe.

3. The ocular blood flow analyzer of claim 1, further comprising:
  a pressure transducer responsive to the fluid supplied to the probe adapted to produce an electrical analog signal representing fluid pressure in the probe.

4. The ocular blood flow analyzer of claim 3, further comprising:
  an analog to digital converter connected to the pressure transducer to convert the electrical analog signal to a digital data stream representing probe pressure as a function of time.

5. The ocular blood flow analyzer of claim 4, further comprising:
  a data acquisition system responsive to the digital data stream to generate and store a representation of probe pressure as a function of time.

6. The ocular blood flow analyzer of claim 1, further comprising:
a signal processor responsive to the probe for generating a signal representing information about blood flow in the eye.

7. The ocular blood flow analyzer of claim 6, in which the information about blood flow in the eye is a volume per unit time blood flow rate in the eye.

8. The ocular blood flow analyzer of claim 6, in which the information about blood flow in the eye is information about pulse rate.

9. The ocular blood flow analyzer of claim 6, in which the information about blood flow in the eye is pulse amplitude information.

10. The ocular blood flow analyzer of claim 6, in which the information about blood flow in the eye is pulsatile volume information.

11. The ocular blood flow analyzer of claim 6, in which the information about blood flow in the eye is a pulsatility index.

12. The ocular blood flow analyzer of claim 6, in which the information about blood flow in the eye is information about pulsatile composite choroidal and retinal ocular blood flow.

13. The ocular blood flow analyzer of claim 1, in which the probe comprises:
a hollow elongated housing defining a pressure chamber having proximal and distal ends inside the housing;
an inlet in the housing adapted to admit fluid from the pump into the pressure chamber;
a port in the housing adapted to communicate with a pressure transducer to allow the pressure transducer to measure the fluid pressure in the housing;
a shaft, having proximal and distal ends, extending from inside the pressure chamber at its proximal end through the housing, the shaft being axially slideable with respect to the housing and defining a sliding bearing between the housing and the shaft;
an axially directed bore formed in the shaft, the bore having proximal and distal ends, the bore being in communication with the fluid in the pressure chamber at its proximal end inside the pressure chamber;
a tip having an open end comprising a venting chamber, secured to the distal end of the shaft, the open end also comprising a nozzle in communication with the distal end of the bore; and
a flexible membrane covering the open end of the tip, the nozzle being arranged to direct fluid from the pressure chamber and the bore in the shaft toward the flexible membrane.

14. The ocular blood flow analyzer of claim 13, further comprising:
an exhaust vent adapted to vent fluid from the venting chamber in the tip.

15. The ocular blood flow analyzer of claim 1, in which the pressure probe produces a pressure signal linearly related to intraocular pressure substantially over a range of intraocular pressures potentially exhibited by patients.

16. The ocular blood flow analyzer of claim 3, further comprising: an electronic circuit that receives a probe pressure signal from the pressure transducer and converts the probe pressure signal to an intraocular pressure signal.

17. The ocular blood flow analyzer of claim 3, further comprising: an electronic circuit responsive to a probe pressure signal from the pressure transducer, the electronic circuit configured to identify a filtered region of interest in the probe pressure signal.

18. The ocular blood flow analyzer of claim 3, further comprising: an electronic circuit, responsive to a probe pressure signal from the pressure transducer, the electronic circuit configured to convert the probe pressure signal into an intraocular pressure signal representing intraocular pressure as function of time in an eye being examined by the ocular blood flow analyzer.

19. The ocular blood flow analyzer of claim 18, further comprising:
an additional electronic circuit responsive to the intraocular pressure signal for generating a signal representing a change in eye volume as a function of time.

20. The ocular blood flow analyzer of claim 18, further comprising:
a filter that removes a DC offset from a region of interest in the intraocular pressure signal.

21. The ocular blood flow analyzer of claim 1, further comprising:
an inflow detector, responsive to the pressure probe, the inflow detector adapted to determine the amount of blood entering the eye for each heartbeat.

22. The ocular blood flow analyzer of claim 1, further comprising:
an outflow detector, responsive to the pressure probe, the outflow detector adapted to determine the amount of blood draining from the eye after each heartbeat.

23. A method of measuring composite ocular blood flow, comprising the steps of:
applying force to an eye with a composite ocular blood flow analyzer of claim 11; and
detecting pressure fluctuations in the composite ocular blood flow analyzer in response to contact of the probe with an eye.

24. The method of measuring composite ocular blood flow of claim 23, further comprising the step of:
producing data relating to blood flow in the eye in response to the pressure fluctuations in the probe.

25. Method of detecting an abnormal condition in a human being, comprising the steps of:
using the composite ocular blood flow analyzer of claim 1 to produce data relating to ocular blood flow in a patient; and
assessing an abnormal condition of a patient in response to the data relating to ocular blood flow.

26. The method of claim 25, in which the abnormal condition is glaucoma.

27. The method of claim 25, in which the abnormal condition is macular degeneration.

28. The method of claim 25, in which the abnormal condition is diabetic retinopathy.

29. The method of claim 25, in which the abnormal condition is ischemic optic neuropathy.

30. The method of claim 25, in which the abnormal condition is retinal venous occlusive disease.

31. The method of claim 25, in which the abnormal condition is retinopathy of prematurity.

32. The method of claim 25, in which the abnormal condition is Alzheimer's disease.

33. The method of claim 25, in which the abnormal condition is carotid occlusive disease.

34. The method of claim 25, in which the abnormal condition is a systemic disease.

35. The ocular blood flow analyzer of claim 4, wherein the analog to digital converter samples the electrical analog signal at a rate of at least 50 Hz.

36. The ocular blood flow analyzer of claim 4, wherein the analog to digital converter samples the electrical analog signal at a rate of at least 100 Hz.

37. The ocular blood flow analyzer of claim 35, in which the analog to digital converter is an at least 14 bit analog to digital converter.

38. The ocular blood flow analyzer of claim 36, in which the analog to digital converter is an at least 14 bit analog to digital converter.

39. The ocular blood flow analyzer of claim 1, further comprising:
a data acquisition system, responsive to the pressure probe, the data acquisition system adapted to collect and store probe pressure data as a function of time.

40. The ocular blood flow analyzer of claim 39, further comprising:
a smoothing circuit responsive to at least a portion of stored probe pressure data, the smoothing circuit adapted to produce a smoothed representation of probe pressure data.

41. The ocular blood flow analyzer of claim 40, in which the smoothing circuit comprises a boxcar filter of predetermined width.

42. The ocular blood flow analyzer of claim 40, further comprising:
a differentiation circuit that differentiates the smoothed representation of probe pressure data; and
a first circuit responsive to the representation of differentiated and smoothed probe pressure data to identify a pulsatile region of interest in the probe pressure data.

43. The ocular blood flow analyzer of claim 42, further comprising:
a second circuit responsive to the first circuit, the second circuit adapted to truncate the smoothed probe pressure data.

44. The ocular blood flow analyzer of claim 39, further comprising: a conversion circuit adapted to convert the probe pressure data to intraocular pressure data in accordance with a predetermined relationship between probe pressure and intraocular pressure.

45. The ocular blood flow analyzer of claim 44, in which the predetermined relationship is:

PP=1.96(IOP)+1.75, where PP is the probe pressure and IOP is the intraocular pressure.

46. The ocular blood flow analyzer of claim 45, further comprising:
a circuit, responsive to the intraocular pressure data, the circuit responsive to the intraocular pressure data adapted to produce a signal representing mean intraocular pressure.

47. The ocular blood flow analyzer of claim 46, in which the circuit that produces a signal representing mean intraocular pressure comprises:
a circuit that fits a first order polynomial to the intraocular pressure data and computes the mean intraocular pressure in light of the intraocular pressure and the first order polynomial.

48. The ocular blood flow analyzer of claim 46, further comprising:
a circuit responsive to the intraocular pressure data that produces flattened, zero-based intraocular pressure data.

49. The ocular blood flow analyzer of claim 48, in which the circuit that produces flattened zero-based intraocular pressure data, comprises:
a circuit that fits a third order polynomial to the intraocular pressure data; and
a circuit that subtracts the third order polynomial from the intraocular pressure data to create a flattened zero-based region of interest in the intraocular pressure data.

50. The ocular blood flow analyzer of claim 44, further comprising:
a peak detector responsive to the intraocular pressure data that identifies positive and negative peaks in the intraocular pressure data.

51. The ocular blood flow analyzer of claim 50, in which the peak detector comprises:
a smoothing circuit that suppresses noise in the intraocular pressure data;
a differentiation circuit that differentiates the smoothed intraocular pressure data;
a boxcar filter that is applied to the differentiated intraocular pressure data that produces an output composed of positive and negative polarities; and
a polarity detector responsive to the boxcar filter that senses whether the boxcar filter output has a positive or negative polarity.

52. The ocular blood flow analyzer of claim 51, in which a change in polarity in the output of the boxcar filter signifies a peak in the intraocular pressure data.

53. The ocular blood flow analyzer of claim 52, in which a change in polarity in the output of the boxcar filter from positive to negative signifies a positive peak in the intraocular pressure data.

54. The ocular blood flow analyzer of claim 52, in which a change in polarity in the output of the boxcar filter from negative to positive signifies a negative peak in the intraocular pressure data.

55. The ocular blood flow analyzer of claim 50, further comprising:
a first averaging circuit that produces a signal related to the average of the positive peaks in the intraocular pressure data; and
a second averaging circuit that produces a signal related to the average of the negative peaks in the intraocular pressure data.

56. The ocular blood flow analyzer of claim 55, further comprising:
a subtraction circuit that subtracts the signals related to the averages of the positive and negative peaks to obtain a pulse amplitude indication.

57. The ocular blood flow analyzer of claim 48, further comprising: an adding circuit that adds the signal representing mean intraocular pressure to the flattened zero-based intraocular pressure signal to obtain a flattened intraocular pressure pulsatile region.

58. The ocular blood flow analyzer of claim 50, further comprising:
a pulse rate determination circuit, responsive to the peaks identified by the peak detector, the pulse rate determination circuit adapted to produce a signal representing a pulse rate.

59. The ocular blood flow analyzer of claim 44, further comprising:
a transformation circuit that converts the intraocular pressure data to change in eye volume data in accordance with a predetermined relationship between intraocular pressure and eye volume.

60. The ocular blood flow analyzer of claim 59, in which the predetermined relationship is:

$\Delta V = -49.8 + 30.2 \ln P + 0.242 P$, where ΔV is the change in eye volume and P is the intraocular pressure.

61. The ocular blood flow analyzer of claim 59, in which the predetermined relationship is:

$$\Delta V = -52.2 + 31.7 \ln P + 0.254 P,$$

where ΔV is the change in eye volume and P is the intraocular pressure.

62. The ocular blood flow analyzer of claim 59, in which the predetermined relationship is:

$$\Delta V = -47.4 + 28.7 \ln P + 0.230 P$$

where ΔV is the change in eye volume and P is the intraocular pressure.

63. The ocular blood flow analyzer of claim 59, further comprising:
  a circuit responsive to the change in volume data for generating an instantaneous rate of change of volume signal d(ΔV)/dt.

64. The ocular blood flow analyzer of claim 63, in which the circuit that generates the instantaneous rate of change of volume signal comprises:
  a smoothing circuit responsive to the change of volume data adapted to suppress noise in the change of volume data and produce a noise suppressed change in volume data.

65. The ocular blood flow analyzer of claim 64, in which the circuit that generates the instantaneous rate of change of volume signal further comprises:
  a differentiator responsive to the smoothing circuit adapted to differentiate the noise suppressed change of volume data.

66. The ocular blood flow analyzer of claim 64, in which the smoothing circuit comprises:
  a boxcar filter of predetermined width responsive to the change of volume data.

67. The ocular blood flow analyzer of claim 64, further comprising:
  a peak detector that identifies positive peaks in the instantaneous rate of change of volume signal d(ΔV)/dt; and
  an averaging circuit responsive to the positive peaks to generate a signal representing a mean instantaneous peak net pulsatile flow parameter.

68. The ocular blood flow analyzer of claim 46, further comprising a screen that displays the mean intraocular pressure.

69. The ocular blood flow analyzer of claim 58, further comprising a screen that displays the pulse rate.

70. The ocular blood flow analyzer of claim 46, further comprising a screen that displays the pulse amplitude.

71. The ocular blood flow analyzer of claim 67, further comprising a screen that displays the peak net pulsatile flow.

72. The ocular blood flow analyzer of claim 44, an acquisition circuit that receives signals representing systolic and diastolic arterial blood pressure; and a circuit that generates a mean perfusion pressure signal in response to the signals representing systolic and diastolic blood pressure.

73. The ocular blood flow analyzer of claim 72, in which the mean perfusion pressure signal generating circuit generates the mean perfusion pressure signal in accordance with the following relationship:

$$\text{mean OPP} = 2.0/3.0*(DBP + 1.0/3.0*(SBP-DBP)) - \text{mean IOP},$$

where OPP is the ocular perfusion pressure, DBP is the diastolic blood pressure, SBP is the systolic blood pressure, and IOP is the intraocular pressure.

74. The ocular blood flow analyzer of claim 44,
  an acquisition circuit that receives signals representing systolic arterial blood pressure; and
  a circuit that generates a signal related to systolic ocular perfusion pressure in response to the signals representing systolic arterial blood pressure.

75. The ocular blood flow analyzer of claim 74, in which the systolic ocular perfusion pressure signal generating circuit generates the systolic perfusion pressure in accordance with the following relationship:

$$\text{systolic OPP} = SBP - \text{mean IOP},$$

where OPP is the ocular perfusion pressure, SBP is the systolic blood pressure, and IOP is the intraocular perfusion pressure.

76. The ocular blood flow analyzer of claim 44,
  an acquisition circuit that receives signals representing diastolic arterial blood pressure; and
  a circuit that generates a signal related to diastolic perfusion pressure in response to the signals representing diastolic blood pressure.

77. The ocular blood flow analyzer of claim 76, in which the diastolic perfusion pressure signal generating circuit generates the diastolic perfusion pressure in accordance with the following relationship:

$$\text{diastolic OPP} = DBP - \text{mean IOP},$$

where OPP is the ocular perfusion pressure, DBP is the diastolic blood pressure, and IOP is the intraocular pressure.

78. The ocular blood flow analyzer of claim 3, further comprising:
  a digital signal processor comprising an analog to digital converter connected to the analog signal from the pressure transducer to convert the analog signal to at least a 100 Hz 14-bit digital data stream representing raw probe pressure as a function of time; and
  a data acquisition system that collects at least about 5-15 seconds of the at least 100 Hz 14-bit raw probe pressure data and stores that raw pressure data in a memory.

79. The ocular blood flow analyzer of claim 5, further comprising:
  a data processor responsive to the stored probe pressure data from the data acquisition system for generating a signal representing intraocular pressure as a function of time.

80. The ocular blood flow analyzer of claim 1, further comprising:
  a digital signal processor, responsive to the pressure probe, the digital signal processor adapted to produce probe pressure data representing raw pneumatic pressure in the probe as a function of time.

81. The ocular blood flow analyzer of claim 80, further comprising:
  an electronic circuit, responsive to the probe pressure data, the electronic circuit adapted to identify a pulsatile region of interest in the probe pressure data.

82. The ocular blood flow analyzer of claim 81, in which the electronic circuit comprises:
  a smoothing circuit responsive to the probe pressure data, the smoothing circuit adapted to create smoothed probe pressure data;
  a differentiation circuit, responsive to the smoothed probe pressure data, the differentiation circuit adapted to differentiate the smoothed probe pressure data; and
  a threshold circuit adapted to detect differentiation circuit output above a first predetermined value and below a second predetermined value, the pulsatile region of interest falling in a time period between the occurrence of the first predetermined value and the occurrence of the second predetermined value.

83. The ocular blood flow analyzer of claim 1, further comprising:
a pressure transducer, responsive to the pressure probe, adapted to produce an electrical analog signal representing fluid pressure in the probe; and
an analog to digital converter, responsive to the pressure transducer, the analog to digital converter adapted to produce samples of probe pressure.

84. The ocular blood flow analyzer of claim 83, in which the analog to digital converter samples pressure in the probe at a rate of at least 50 to 200 Hz.

85. The ocular blood flow analyzer of claim 84, in which the probe pressure samples are at least 14-bit samples.

86. The ocular blood flow analyzer of claim 80, in which the probe pressure data is at least 5-15 seconds of 14-bit samples taken at a rate of at least 50-200 Hz.

87. The ocular blood flow analyzer of claim 1, further comprising:
an electronic circuit, responsive to the pressure probe, adapted to produce data representing ocular blood flow as a function of time.

88. The ocular blood flow analyzer of claim 1, further comprising:
an electronic circuit, responsive to the pressure probe, adapted to produce data representing intraocular pressure as a function of time.

89. The method of claim 25, in which the abnormal condition is retinal arterial occlusive disease.

90. The method of claim 25, in which the abnormal condition is retinitis pigmentosa.

91. The method of claim 25, in which the abnormal condition is burned skin.

92. The method of claim 25, in which the abnormal condition is cerebral vascular flow/edema or pressure associated with traumatic brain injury.

93. The method of claim 25, in which the abnormal condition is intracranial pressure in newborns.

94. The apparatus of claim 1, in which the pneumatic fluid supply further comprises:
a brushless DC electric motor connected to the pump to control the pressure of the fluid from the output of the pump.

\* \* \* \* \*